(12) United States Patent
Staats et al.

(10) Patent No.: US 6,270,758 B1
(45) Date of Patent: Aug. 7, 2001

(54) SUBSTANTIALLY NON-TOXIC BIOLOGICALLY ACTIVE MUCOSAL ADJUVANTS IN VERTEBRATE SUBJECTS

(75) Inventors: Herman F. Staats; Barton F. Haynes; Dhavalkumar D. Patel; Gregory D. Sempowski, all of Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/168,910

(22) Filed: Oct. 8, 1998

(51) Int. Cl.[7] .......................... A61K 45/00; A61K 39/00; A61K 47/00; C07K 1/00; C07K 14/00

(52) U.S. Cl. ..................... 424/85.2; 424/85.2; 424/184.1; 424/198.1; 424/278.1; 530/351

(58) Field of Search ............................. 424/278.1, 184.1, 424/198.1, 85.2, 85.1; 530/351; 514/2

(56) References Cited

U.S. PATENT DOCUMENTS

| | | | |
|---|---|---|---|
| 4,935,343 | 6/1990 | Allison et al. | 435/7 |
| 5,008,374 | 4/1991 | Nakai et al. | 530/351 |
| 5,206,014 | 4/1993 | Nencioni et al. | 424/88 |
| 5,210,072 | 5/1993 | Chedid et al. | 514/8 |
| 5,266,311 | 11/1993 | Cerrati et al. | 424/85.2 |
| 5,334,379 | 8/1994 | Pillai et al. | 424/85.2 |
| 5,342,614 | 8/1994 | Nakai et al. | 424/85.2 |
| 5,342,615 | 8/1994 | Nakai et al. | 424/85.2 |
| 5,371,204 | 12/1994 | Nakai et al. | 536/23.5 |
| 5,437,988 | 8/1995 | Bellini et al. | 435/69.52 |
| 5,474,899 | 12/1995 | Lisi | 435/7.1 |
| 5,543,140 | 8/1996 | Nakai et al. | 424/85.2 |
| 5,702,698 | 12/1997 | Nakai et al. | 424/85.2 |
| 5,728,571 | 3/1998 | Bellini et al. | 435/252.31 |

FOREIGN PATENT DOCUMENTS

| | | | |
|---|---|---|---|
| 353516 | 9/1994 | (EP) | C12N/15/25 |
| 761688 | 3/1997 | (EP) | C07K/16/24 |
| 810285 | 12/1997 | (EP) | C12N/15/24 |
| 63-258595 | 10/1988 | (JP) | C12P/21/00 |
| 5-244990 | 9/1993 | (JP) . | |
| 93/01929 | 10/1994 | (NL) . | |
| 88/06843 | 9/1988 | (WO) | A01N/61/00 |
| 91/01143 | 2/1991 | (WO) | A61K/39/39 |
| 91/13986 | 9/1991 | (WO) | C12N/15/25 |
| 92/03574 | 3/1992 | (WO) | C12Q/1/68 |
| 94/00491 | 1/1994 | (WO) | C07K/13/00 |
| 9607673 | 3/1996 | (WO) | C07K/14/52 |

OTHER PUBLICATIONS

Gao et al. Vaccine, vol. 13, No. 9, pp. 871–877, Jun. 1995.*
Abraham et al. The Journal of Immunology, vol. 149, No. 11, pp. 3719–3726, Dec. 1992.*
Giannarini et al., "Decrease of Allergen–specific T–cell Response Induced by Local Nasal Immunotherapy", vol. 28, *Clinical and Experimental Allergy*, pp. 404–412 (1998).
Pockley et al., "In Vivo Adjuvant Effect of Interleukins 5 and 6 on Rat Tear IgA Antibody Responses", vol. 73, *Immunology*, pp. 19–23 (1991).
O'Hagan, "Recent Advances in Vaccine Adjuvants for Systemic and Mucosal Administration", vol. 49, *J. Pharm Pharmacol*, pp. 1–10 (1997).
Kramer et al., "Cytokine Mediated Effects in Mucosal Immunity", vol. 73, *Immunology and Cell Biology*, pp. 389–396 (1995).
Nash et al., "Recombinant Cytokines as Immunological Adjuvants", vol. 71, *Immunology and Cell Biology*, pp. 367–379 (1993).
Lin et al., "Present Status of the Use of Cytokines as Adjuvants with Vaccines to Protect Vaccines to Protect Against Infectious Diseases", vol. 21, *Clinical Infectious Diseases*, pp. 1439–1449 (1995).
Li et al., "Nasal Tolerance to Experimental Autoimmune Myasthenia Gravis: Tolerance Reversal by Nasal Administration of Minute Amounts of Interferon–γ", vol. 87 *Clinical Immunology and Immunopathology*, pp. 15–22 (1998).
Marinaro et al., "Oral but Not Parenteral Interleukin (IL)–12 Redirects T Helper 2 (Th2)–type Responses to an Oral Vaccine Without Altering Mucosal IgA Responses", vol. 185, No. 3, *J Exp. Med.*, pp. 415–427 (Feb. 3, 1997).
Xiao et al., "Suppression of Acute and Protracted–relapsing Experimental Allergic Encephalomyelitis by Nasal Administration of Low–dose IL–10 in Rats", vol. 84, *Journal of Neuroimmunology*, pp. 230–237 (Apr. 15, 1998) (Abstract).
Fujimara et al., "Effect of Thromboxane A2 Antagonists on Bronchial Hyperresponsiveness Induced Immediately after Interleukin–8 Inhalation in Guinea–pigs", vol. 122, *British Journal of Pharmacology*, pp. 1015–1020 (1997).
Sarkar, "Drug Metabolism in the Nasal Mucosa," *Pharm. Res.*, p. 1–9, (Jun. 12, 1992).
Pontiroli et al., "Nasal Administration of Glucagon and Human Calcitonin to Healthy Subjects: A Comparison of Powders and Spray Solutions and of Different Enhancing Agents," *European Journal of Clinical Pharmacology*, p. 427–430, (Jun. 12, 1989).
Elson et al., "Mucosal Adjuvants," *Handbook of Mucosal Immunology*, Academic Press, Inc. (San Diego), p. 391–402, (Jun. 12, 1994).

(List continued on next page.)

*Primary Examiner*—Gary L. Kunz
*Assistant Examiner*—Robert S. Landsman
(74) *Attorney, Agent, or Firm*—Jenkins & Wilson, P.A.

(57) ABSTRACT

A method of eliciting an immune response against an antigen in a vertebrate subject, the method comprising the steps of providing an antigen-adjuvant composition comprising the antigen and a substantially non-toxic adjuvant molecule having biological activity in mucosal tissues, and administering said antigen-adjuvant composition to the vertebrate subject in a manner such that initial contact occurs in mucosal tissue of the vertebrate subject, whereby an immune response is elicited. Cytokines are preferred adjuvants. Preferred cytokines are interleukin-1α (IL-1α) and interleukin-1β (IL-1β).

64 Claims, 4 Drawing Sheets

OTHER PUBLICATIONS

Reiss, T. and Strauss, E., "Vaccines–Patenting Dynamics of a Powerful Healthcare Tool," Exp. Opin. Ther. Patents, vol. 8 (No. 8), p. 951–958, (Jun. 12, 1998).

Elson, "Cholera Toxin as a Mucosal Adjuvant," Mucosal Vaccines, Academic Press (New York), p. 59–72, (Jun. 12, 1996).

Jenkins, "Mucosal Vaccine Delivery," Exp. Opin. Ther. Patents, p. 255–262, (Jun. 12, 1999).

Lillard et al., "Lymphotactin Acts as an Innate Mucosal Adjuvant," J. Immuno., vol. 162 (No. 4), p. 1959–1965, (Feb. 15, 1999).

MRSNY, "Adjuvants and Delivery Issues Related to Immunization: A Survey of the Recent Patent Literature," J. of Drug Targeting, vol. 6 (No. 4), p. 243–249, (Jun. 12, 1998).

Callard et al, The Cytokine Facts Book, Academic press, Harcourt & Co, publishers, p. 241, 1994.*

* cited by examiner

SUBSTANTIALLY NON-TOXIC BIOLOGICALLY ACTIVE MUCOSAL ADJUVANTS IN VERTEBRATE SUBJECTS

GRANT STATEMENT

This work was supported by National Institute of Health (NIH) grant 5 UO1 Al35351-04. The United States Government has certain rights in the invention.

TECHNICAL FIELD

The present invention relates to the use of substantially non-toxic, biologically active molecules as mucosal adjuvants in vertebrate subjects. More particularly, the present invention relates to the use of cytokines, such as interleukin-1α (IL-1α) and interleukin-1β (IL-1β), as mucosal adjuvants in vertebrate subjects.

Table of Abbreviations

| | |
|---|---|
| CT | cholera toxin |
| CTL | cytotoxic T lymphocyte(s) |
| DC | dendritic cells |
| DTH | delayed-type hypersensitivity |
| EGF | epithelial growth factor |
| FKN | fractalkine |
| GALT | gut-associated lymphoid tissue |
| GCSF | granulocyte colony stimulating factor |
| GM-CSF | granulocyte-macrophage colony stimulating factor |
| HIV | human immunodeficiency virus |
| HSV | herpes simplex virus |
| IDC | immature dendritic cells |
| IFN | interferon |
| Ig | immunoglobulin |
| IgA | immunoglobulin A |
| IGF-1 | insulin-like growth factor |
| IgG | immunoglobulin G |
| IL | interleukin |
| LARC | liver and activation regulated chemokine |
| LT | heat-labile toxin |
| MDC | macrophage derived chemokine |
| PARC | pulmonary and activation regulated chemokine |
| PT | pertussis toxin |
| RSV | respiratory syncytial virus |
| SLC | secondary lymphoid-tissue chemokine |
| TARC | thymus and activation regulated chemokine |
| TGF | transforming growth factor |
| Th 1 | T helper cell type 1 |
| Th 2 | T helper cell type 2 |
| TNF | tumor necrosis factor |
| TT | tetanus toxoid |

BACKGROUND ART

Antigen-specific mucosal immune responses, such as secretory IgA production and mucosal cytotoxic T lymphocyte (CTL) responses, may play an important role in host protection against infectious agents that infect via the mucosal surfaces of the host, including human immunodeficiency virus (HIV), herpes simplex virus (HSV), respiratory syncytial virus (RSV), *Bordetella pertussis*, and *Salmonella typhimurium*. See Ogra, in *Mucosal Vaccines*. p. 3 (1996).

A major obstacle in the path of developing effective mucosal vaccines is the identification of a safe and effective mucosal adjuvant. Indeed, mucosal immunization with soluble protein or peptide immunogens in the absence of a mucosal adjuvant tends to induce a state of antigen-specific immunological tolerance known as oral tolerance, or more appropriately, mucosally-induced tolerance. See e.g., Mowat, in *Handbook of Mucosal Immunology*. p. 185 (1994); Husby et al., *Journal of Immunology* 152:4663 (1994); Staines et al., *Clinical & Experimental Immunology* 103:368 (1996).

In contrast, mucosal immunization with soluble protein antigens or peptides co-administered with a mucosal adjuvant such as cholera toxin (CT), pertussis toxin (PT), or heat-labile toxin (LT) may induce potent systemic and mucosal, humoral and cell-mediated immune responses. Indeed, the most potent and best-studied mucosal adjuvant is cholera toxin (CT), Elson et al., in *Handbook of Mucosal Immunology*, p. 391 (1994). However, CT is likely unsafe for use as a mucosal adjuvant in humans because as little as 5 micrograms (μg) of CT causes massive diarrhea when intragastrically administered to human volunteers. Levine et al., *Microbiological Reviews* 47:510 (1983). Moreover, in some cases the use of CT as a mucosal adjuvant in research animals has been associated with the production of antigen-specific IgE responses and lethal anaphylactic reactions. See e.g., Snider et al., *J Immunol* 153:647 (1994); Marinaro et al., *J Immunol* 155:4621 (1995).

To repress the toxicity associated with toxin adjuvants, mutant CT, LT, and PT molecules have been produced that exhibit reduced or undetectable toxic activity while maintaining mucosal adjuvant activity. O'Hagan, *Journal of Pharmacy and Pharmacology* 49:1 (1997). Although these molecules possess potent adjuvant activity with reduced toxicity, they maintain immunogenic properties when administered to experimental animals. See e.g., Douce et al., *Infection & Immunity* 65:2821 (1997). Thus, the immunogenicity of these mutant toxin molecules also prevents their widespread and repeated use as mucosal adjuvants in that pre-existing immunity to CT reduces their adjuvant activity. Wu et al., *Vaccine* 12:215 (1994).

PCT Publication No. WO 91/01143 to Pillai et al. describes interleukin (IL)-containing vaccine compositions which comprise a mixture of antigen and an adjuvant amount of an IL adsorbed onto a mineral in suspension, and a preservative. The mineral is described as preferably being alum. Alum is described as stabilizing the biological activity of the IL. Exemplary IL's includes IL-1α, IL-1β, IL-2, IL-3, IL-4, IL-5, IL-6 and IL-7. It is noted that in the absence of alum, IL's have short half lives. Carbohydrate-containing units found uniquely on cancer cells or found associated with allergens are particularly described antigens. However, the problems associated with oral or mucosally-induced tolerance of antigens are not addressed.

U.S. Pat. No. 5,334,379 issued to Pillai et al. on Aug. 2, 1994 describes cytokine and hormone carriers for conjugate vaccines. The antigens described in this patent are bound or genetically fused with a cytokine, lymphokine, hormone or growth factor having immunomodulating activity. Particularly contemplated antigens include the carbohydrate-containing antigens often present in bacteria. Exemplary cytokines, lymphokines and hormones include IL-1α, IL-1β, IL-2, prolactin, EGF, TGF, GM-CSF, GCSF, IGF-1, somatotropin, or insulin. The conjugates may be prepared by any of the known complex, biologically compatible methods for coupling carbohydrate-containing antigens or other antigens to carriers. Covalent coupling is described as a preferred method. Indeed, Examples 1 and 2 describe the elaborate reactions required to conjugate or bind the antigens to the cytokine, lymphokine, hormone or growth factor. However, the problems associated with oral or mucosally-induced tolerance of antigens are not addressed.

A recent review article by Kramer et al. entitled "Cytokine Mediated Effects in Mucosal Immunology" in *Immunology*

& *Cell Biology* 73:389 (1995) discusses the role of IL-5, IL-6, and TGF-β in the induction of mucosal IgA responses. Particularly, this paper discusses published results from experiments done in mice lacking a functional IL-5 or IL-6 gene. It also discusses papers which describe the co-expression of IL-5 or IL-6 with vaccine antigen in a live vaccinia virus, and which describe that the co-expression of IL-5 or IL-6 enhances mucosal IgA responses. However, the article then suggests that complex delivery methods will be required to deliver the cytokines to the mucosa.

Another recent review article by O'Hagan entitled "Recent Advances in Vaccine Adjuvants for Systemic and Mucosal Adjuvants" in the *Journal of Pharmacy and Pharmacology* 49:1 (1997) discusses the state of the use of adjuvants for systemic and mucosal administration. This review article discusses a number of different adjuvants for use with mucosally administered vaccines including particulates (i.e. microspheres), oil-in-water emulsions, and mutated forms of heat-labile enterotoxin (LT) and cholera toxin (CT). But, this article does not mention the use of cytokines as mucosal vaccine adjuvants.

A journal article by Lin et al. entitled "Present Status of the Use of Cytokines as Adjuvants with Vaccines to Protect Against Infectious Diseases" in *Clinical Infectious Diseases* 21:1439 (1995) discusses the use of select cytokines (IL-1, IL-2, IL-3, IL-4, IL-6, IL-7, and IL-12; tumor necrosis factor (TNF); interferon; and GM-CSF as adjuvants. But, the use of cytokines as mucosal vaccine adjuvants is not suggested in this article.

A journal article by Nash et al. entitled "Recombinant Cytokines as Immunological Adjuvants", *Immunology and Cell Biology* 71:367 (1993) discusses the use of recombinant ovine IL-2, IL-1α and tumor necrosis factor-α (TNF-α) as adjuvants. The formulation of IL-1α with aluminum hydroxide (alum) is mentioned for use as an adjuvant capable of enhancing secondary humoral responses. But, there is no suggestion of mucosal administration of IL-1α.

Despite the substantially non-toxic and biologically active nature of cytokines like the interleukins, the recognized uses of such molecules as adjuvants require complex conjugation or formulation techniques. Moreover, even in view of the potential benefits of mucosal immunization, a solution to the oral tolerance problem described above has yet to be identified. Thus, a safe, effective and easily formulated mucosal adjuvant is needed to aid the development of effective mucosal vaccines.

SUMMARY OF THE INVENTION

In accordance with the present invention, a method of eliciting an immune response against an antigen in a vertebrate subject is provided. The method comprises the steps of providing an antigen-adjuvant composition comprising the antigen and a substantially non-toxic adjuvant molecule or molecules having biological activity in mucosal tissues, and administering said antigen-adjuvant composition to the vertebrate subject in a manner such that initial contact occurs in mucosal tissue of the vertebrate subject, whereby an immune response is elicited. Preferably, the immune response comprises a systemic and/or mucosal immune response.

Accordingly, it is an object of the present invention to provide a functional method of mucosal immunization.

It is another object of the present invention to address oral tolerance in mucosal immunization by providing a safe and effective mucosal adjuvant.

It is still another object of the present invention to provide a mucosal adjuvant that is easily formulated yet substantially non-toxic to the subject to be immunized.

Some of the objects of the invention having been stated hereinabove, other objects will become evident as the description proceeds, when taken in connection with the accompanying drawings as best described hereinbelow.

DETAILED DESCRIPTION OF THE INVENTION

In accordance with the present invention, a method of eliciting an immune response against an antigen in a vertebrate subject is provided. The method comprises the steps of providing an antigen-adjuvant composition comprising the antigen and a substantially non-toxic, biologically active adjuvant molecule having adjuvant and other biological activity in mucosal tissues, and administering said antigen-adjuvant composition to the vertebrate subject in a manner such that initial contact occurs in mucosal tissue of the vertebrate subject, whereby an immune response is elicited. Mucosal immunization with soluble protein antigen alone induces antigen-specific (oral) tolerance while mucosal immunization with antigen in the presence of a mucosal adjuvant according to the present invention induces antigen-specific systemic and mucosal humoral and cell-mediated immune responses. Thus, the present invention addresses the problem of mucosal, or oral, antigen-specific tolerance.

While the following terms are believed to have well defined meanings in the art, the following definitions are set forth to facilitate explanation of the invention.

The term "immune system" includes all the cells, tissues, systems, structures and processes, including non-specific and specific categories, that provide a defense against "non-self" molecules, including potential pathogens, in a vertebrate subject.

As is well known in the art, the non-specific immune system includes phagocytositic cells such as neutrophils, monocytes, tissue macrophages, Kupffer cells, alveolar macrophages, dendritic cells and microglia. The specific immune system refers to the cells and other structures that impart specific immunity within a host. Included among these cells are the lymphocytes, particularly the B cell lymphocytes and the T cell lymphocytes. These cells also include natural killer (NK) cells. Additionally, antibody-producing cells, like B lymphocytes, and the antibodies produced by the antibody-producing cells are also included within the term "immune system".

The term "substantially non-toxic" is meant to refer to adjuvant molecules which cause few detrimental effects when administered to a vertebrate subject. Examples of detrimental effects include the nausea and anaphylactic shock observed through the use of standard adjuvants like cholera toxin. Thus, the term "substantially non-toxic" can be quantified by comparison to cholera toxin as a known standard. Further, "substantially non-toxic" can mean without prolonged or major side effects including weight loss and prolonged fever, and including, but not limited to, the flu-like symptoms such as fever, prolonged muscle or joint pain, or hypotension (shock), that are observed with some vaccinations currently used in the art.

By way of further explanation of the term "substantially non-toxic" as used in accordance with the present invention, two of the adjuvants described herein below, IL-1α and IL-1β, have both been used in Phase I/II clinical trials in humans. For these human trials, IL-1α and IL-1β were used in cancer patients undergoing chemotherapy. The IL-1 was usually administered by IV drip on a daily basis. The IL-1 was found to have side effects that included flu-like symptoms, including: fever, chills and rigors, nausea, vomiting, fatigue, headache, myalgia and arthralgia, hypotension, tachycardia, abdominal pain, peripheral vein phlebitis, confusion and somnolence, dyspnea, edema and prerenal axotemia. See e.g., Veltri et al., *Stem Cells* 14:164–176 (1996); Rinehart et al., *Can. Invest.* 15:403–410 (1997); Verschraegen et al., *Eur. J. Can.* 32A:1609–1611 (1996); Janik et al., *J. Nat. Can. Inst.* 88:44–49 (1996); Weisdorf et al., *Blood* 84:2044–2049 (1994).

While applicants do not wish to be bound to any particular theory of operation of the invention, it is believed that many of the side effects are due to IV administration and exposure of the entire body to IL-1. Thus, applicants contemplate that intramucosal (e.g. nasal) administration of the cytokines limits systemic toxicity because the cytokines, as well as other adjuvants as described herein, are administered locally. Also, as described herein below, in mice, when using a "high" dose of IL-1 (e.g., 4 μg for 3 doses at weekly intervals), obvious toxic effects such as ruffled fur or obvious weight loss in the mice were not observed. In other studies in rabbits, which are also referred to below, nasal administration of 80 μg of IL-1β induced a 1.0–1.5° C. fever by 3–4 hours after nasal administration. But, the body temperature returned to normal within 24 hours and no weight loss was observed. Thus, the term "substantially non-toxic" is also meant to encompass the observed absence of systemic toxicity when the adjuvants of the present invention are administered intramucosally as compared to the systemic toxicity observed when contemplated adjuvants of the present invention are administered intravenously as a component of chemotherapy as described above.

The terms "mucosal administration" and "intramucosal administration" are meant to refer to a mode of administration whereby an antigen-adjuvant composition according to the present invention is administered in a manner such that initial contact occurs in mucosal tissue of the vertebrate subject. Examples of mucosal tissue include the nasal membranes, vaginal membranes, rectal membranes and gastric membranes. Thus, contemplated administration techniques according to the methods of the present invention include intranasal administration, intravaginal administration and intrarectal administration, among other intramucosal administration techniques.

The term "biological activity" is meant to refer to a molecule having a biological or physiological effect in a vertebrate subject. Adjuvant activity is an example of a biological activity. Activating or inducing production of other biological molecules having adjuvant activity is also a contemplated biological activity.

The term "adjuvant activity" is meant to refer to a molecule having the ability to enhance or otherwise modulate the response of a vertebrate subject's immune system to an antigen.

The term "immune response" is meant to refer to any response to an antigen orantigenic determinant by the immune system of a vertebrate subject. Exemplary immune responses include humoral immune responses (e.g. production of antigen-specific antibodies) and cell-mediated immune responses (e.g. lymphocyte proliferation), as defined herein below.

The term "systemic immune response" is meant to refer to an immune response in the lymph node-, spleen-, or gut-associated lymphoid tissues wherein cells, such as B lymphocytes, of the immune system are developed. For example, a systemic immune response can comprises the production of serum IgG's. Further, systemic immune response refers to antigen-specific antibodies circulating in the blood stream and antigen-specific cells in lymphoid tissue in systemic compartments such as the spleen and lymph nodes. In contrast, the gut-associated lymphoid tissue (GALT) is a component of the mucosal immune system since antigen-specific cells that respond to gut antigens/pathogens are induced and detectable in the GALT.

The term "mucosal immune response" is meant to refer to an immune response in the mucosal tissues of a vertebrate subject. The mucosal immune response can comprise production of IgA's, particularly secretory IgA's, in mucosal tissue at a location in the vertebrate subject away from the site of mucosal administration of the antigen-adjuvant composition according to the present invention.

The terms "humoral immunity" or"humoral immune response" are meant to refer to the form of acquired immunity in which antibody molecules are secreted in response to antigenic stimulation.

The terms "cell-mediated immunity" and "cell-mediated immune response" are meant to refer to the immunological defense provided by lymphocytes, such as that defense provided by T cell lymphocytes when they come into close proximity to their victim cells. A cell-mediated immune response also comprises lymphocyte proliferation. When "lymphocyte proliferation" is measured, the ability of lymphocytes to proliferate in response to specific antigen is measured. Lymphocyte proliferation is meant to refer to B cell, T-hel per cell or CTL cell proliferation.

The term "CTL response" is meant to refer to the ability of an antigen-specific cell to lyse and kill a cell expressing the specific antigen. Standard, art-recognized CTL assays are performed to measure CTL activity.

Following long-standing patent law convention, the terms "a" and "an" mean "one or more" when used in this application, including the claims.

In accordance with the present invention, the adjuvant may optionally be selected from the group including, but not limited to, cytokines, chemokines, growth factors, angiogenic factors, apoptosis inhibitors, and combinations thereof. When a cytokine is chosen as an adjuvant, the cytokine may be selected from the group including, but not limited to, interleukins including IL-1, IL-1α, IL-1β, IL-2, IL-5, IL-6, IL-12, IL-15 and IL-18; transforming growth factor-beta (TGFβ); granulocyte macrophage colony stimulating factor (GM-CSF); interferon-gamma (IFNα); or other cytokine which has adjuvant activity.

Combinations of cytokines are also contemplated for use in accordance with the methods of the present invention, as presented in the Examples below. Additionally, a particularly contemplated embodiment comprises the use of IL-12 and IL-18 in combination as a mucosal adjuvant in accordance with the methods of the present invention. When cytokines are used in combination, contemplated dosage ranges comprise about 0.3 µg/ml to about 50 µg/ml, with respect to each cytokine. Additional contemplated dosages ranges are described below.

Portions of cytokines, or muteins or mimics of cytokines (or combinations thereof), having adjuvant activity or other biological activity can also be used in the methods of the present invention.

When a chemokine is chosen as an adjuvant, the chemokine may optionally be selected from a group including, but not limited to, LARC, PARC, MDC, TARC, SLC and FKN. When an apoptosis inhibitor is chosen as an adjuvant, the apoptosis inhibitor may optionally be selected from the group including, but not limited to, toso, inhibitors of caspase-8, and combinations thereof. When an angiogenic factor is chosen as an adjuvant, the angiogenic factor may optionally be selected from the group including, but not limited to, a basic fibroblast growth factor (FGF), a vascular endothelial growth factor (VEGF), a hyaluronan (HA) fragment, and combinations thereof. Indeed, plus (+) and minus(-) angiogenic factors may be chosen as adjuvants.

Other examples of substantially non-toxic, biologically active mucosal adjuvants of the present invention include hormones, growth factors, or biologically active portions thereof. Such hormones, growth factors, or biologically active portions thereof can be of human, bovine, porcine, ovine, canine, feline, equine, or avian origin, for example, and can be tumor necrosis factor (TNF), prolactin, epidermal growth factor (EGF), granulocyte colony stimulating factor (GCSF), insulin-like growth factor (IGF-1), somatotropin (growth hormone) or insulin, or any other hormone or growth factor whose receptor is expressed on cells of the immune system.

Cytokines, chemokines, growth factors, angiogenic factors, apoptosis inhibitors and hormones can be obtained from any suitable source. They can be produced by recombinant DNA methodology. For example, the genes encoding several human interleukins have been cloned and expressed in a variety of host systems, permitting the production of large quantities of pure human interleukin. Further, certain T lymphocyte lines produce high levels of interleukin, thus providing a source of the cytokine.

The antigen-adjuvant compositions are preferably administered in a pharmaceutically acceptable vehicle. The preferred vehicle is physiological saline; but, distilled water may also be used as a vehicle. More preferably, the antigen-adjuvant composition is free of mineral adjuvants, preservatives or stabilizers, such as alum. Also preferably, the antigen-adjuvant composition is not conjugated. Rather, the antigen and adjuvant are simply dissolved and/or suspended in the vehicle.

In accordance with the present invention, antigen is intramucosally administered in combination with a substantially non-toxic, biologically active adjuvant preferably at weekly or biweekly intervals for a total of three (3) immunizations in order to stimulate a "protective" immune response. A protective immune response is an immune response sufficient to protect the immunized organism against toxic products of bacteria (tetanus toxin, cholera toxin, E. coli labile toxin, diphtheria toxin, pertussis toxin) as well as against productive infection by a particular pathogen or pathogens to which the vaccine is directed.

Stated differently, the antigen-adjuvant composition may optionally be administered once a week over a period of one to three weeks or once every two weeks over a period of two to six weeks. Alternatively, the antigen-adjuvant composition may be administered once during a first week, and then antigen only may be administered as a booster immunization once a week over a period of one to two weeks following the first week. Further, the antigen-adjuvant composition may optionally be administered once during a first biweekly period, and then antigen only may be administered as a booster immunization once every two weeks over a period of two to four weeks following the first biweekly period.

For example, IL-1α or IL-1β function as mucosal adjuvants when co-administered with antigen during the first immunization. When using IL-1α or IL-1β as a mucosal adjuvant, two additional booster immunization with antigen only sufficiently bolstered the desired level of immune response. The IL-1α or IL-1β adjuvants are preferably present in the antigen-adjuvant composition in an amount ranging from about 10 to about 1000 micrograms per kilogram body weight of the vertebrate subject. More preferably, the IL-1α or IL-1β adjuvant is present in the antigen-adjuvant composition in an amount ranging from about 50 to about 500 micrograms per kilogram body weight of the vertebrate subject. Even more preferably, the IL-1α or IL-1β adjuvant is present in the antigen-adjuvant composition in an amount ranging from about 60 to about 200 micrograms per kilogram body weight of the vertebrate subject.

Optionally, the IL-1β may comprise recombinant IL-1β. In such a case, the recombinant IL-1β may optionally be present in an amount ranging from about 1 to about 100 milligrams per kilogram body weight of the vertebrate subject. More preferably, the recombinant IL-1β is present in the antigen-adjuvant composition in an amount ranging from about 5 to about 50 milligrams per kilogram body weight of the vertebrate subject. Even more preferably, the recombinant IL-1β is present in the antigen-adjuvant composition in an amount ranging from about 10 to about 20 milligrams per kilogram body weight of the vertebrate subject.

The amount of adjuvant employed in the methods of the present invention will vary depending upon the identity of the antigen employed. Adjustment and manipulation of the adjuvant dosage ranges described above for adaptation to a variety of antigens is within the ability of those skilled in the art. The adjuvant-antigen compositions, or vaccines, of the present invention are intended for use in the treatment of vertebrate subjects, including both immature and adult warm-blooded animals. Exemplary warm blooded vertebrate subjects include mammals and birds. Mammals are preferred subjects, with humans comprising a most preferred subject. Indeed, in accordance with the present invention, any vaccine against infection wherein protection at mucosal sites is needed can be formulated for administration to humans or other warm blooded vertebrate animals. Further, the use of the present methods is not limited to prophylactic applications; therapeutic applications are also contemplated (e.g., AIDS prophylaxis and therapy), as well as immune focusing to alter growth, productivity or reproduction.

Certain types of immune responses are more readily produced in accordance with the methods of the present invention as compared to prior art methods. For example, a preferred systemic immune response according to the present invention comprises the production of antigen-specific IgG's at a titer of at least about 1:10,000, with a more preferred titer comprising at least about 1:20,000. As would be apparent to one having ordinary skill in the art, a titer of at least about 1:10,000 or a titer of at least about 1:20,000, for example, means that there remains a detectable quantity of antigen-specific antibody (or Ig) in an ELISA assay after preparing a 1:10,000 dilution, or 1:20,000 dilution, of a sample, respectively.

A preferred mucosal immune response according to the present invention comprises production of IgA's in mucosal tissue in the vertebrate subject at a site removed from the site of administration of the adjuvant. Indeed, as set forth in the Examples presented herein below, without the administration of an adjuvant in accordance with the present invention, no mucosal IgA responses are typically observed in a subject. Moreover, for some antigens administered in accordance with methods of the present invention, the antigen-specific IgA's are produced at a titer of at least about 1:100. Additionally, for other antigens administered in accordance with methods of the present invention, the antigen-specific IgA's are produced at a titer of at least about 1:500. As would be apparent to one having ordinary skill in the art, a titer of at least about 1:100 or a titer of at least about 1:500, for example, means that there remains a detectable quantity of antigen-specific antibody (or Ig) in an ELISA assay after preparing a 1:100 dilution or 1:500 dilution of a sample, respectively.

A particularly desired cell-mediated immune response comprises lymphocyte proliferation. More particularly, the desired lymphocyte proliferation is further characterized by at least about a ten (10)-fold increase in lymphocytes as compared to an unimmunized state. Even more particularly, lymphocyte proliferation is further characterized by at least about a fifty (50)-fold increase in lymphocytes as compared to an unimmunized state.

IL-1α and IL-1β are preferred examples of the mucosal adjuvants of the present invention. IL-1α and IL-1β serve as adjuvants for a variety of immune responses, including: antigen-specific serum IgG, vaginal IgA, systemic delayed-type hypersensitivity (DTH) responses, and lymphocyte proliferative responses, in cells isolated from the spleen. Indeed, the data presented hereinbelow indicates that the cytokines act as adjuvants to enhance 1) antigen-specific antibody (systemic IgG, mucosal IgA) and 2) cell-mediated immunity by lymphocyte proliferation and delayed-type hypersensitivity (DTH). Thus, according to the present invention, IL-1α and IL-1β are used as mucosal adjuvants to induce antigen-specific IgA (>ten (10) fold enhancement over the IgA response induced in the absence of adjuvant; two to four (2–4) fold enhancement over the IgA response induced when using CT as an adjuvant) that is detectable at a site removed from the site of immunization. More particularly, after intranasal immunization in a mammalian test subject, antigen-specific IgA were detected in secretions of the female reproductive tract. No toxic effects, such as anaphylaxis, were noticed with the use of IL-1(α and β) as a mucosal adjuvant. Such an adjuvant is useful for vaccine-mediated protection against a variety of pathogens. More particularly, such an adjuvant is useful for vaccine-mediated protection against pathogens that infect via the mucosal surfaces of the host, such as HIV.

Suitable antigens which can be used in the antigen-adjuvant compositions of the present invention include soluble antigens, such as proteins, peptides, hormones and glycoproteins. Antigens of particular interest are viral, fungal, parasite or bacterial antigens, allergens, auto-immunity related antigens, or tumor-associated antigens. The antigens can be obtained from natural sources or they can be produced by recombinant DNA technology or by other artificial means. Particular antigens contemplated for use according to the present invention are set forth in the Examples presented below.

Among the bacterial antigens of interest are those associated with the human and animal bacterial pathogens including, but not limited to for example, typable and nontypable *Haemophilus influenzae, Escherichia coli, Neisseria meningitidis, Streptococcus pneumoniae, Streptococcus pyogenes, Branhamella catarrhalis, Vibrio cholerae, Corynebacteria diphtheriae, Neisseria gonorrhoeae, Bordetella pertussis, Pseudomonas aeruginosa, Staphylococcus aureus, Klebsiella pneumoniae* and *Clostridium tetani*. Some specific bacterial antigens include bacterial surface and outer membrane proteins (e.g. from *Haemophilus influenzae, Neisseria meningitidis, Neisseria gonorrhoeae* or *Branhamella catarrhalis*) and bacterial surface proteins (e.g. the M protein from *Streptococcus pyogenes*.).

Viral antigens from pathogenic viruses include but are not limited to, HIV (types I and II), human T-cell leukemia virus (types I, II and III), RSV, hepatitis A, hepatitis B, hepatitis C, non-A and non-B hepatitis virus, herpes simplex virus (types I and II), cytomegalovirus, influenza virus, parainfluenza virus, poliovirus, rotavirus, coronavirus, rubella virus, measles virus, varicella, Epstein Barr virus, adenovirus, papilloma virus and yellow fever virus.

Several specific viral antigens of these pathogenic viruses include the F protein (described in WO89/02935 by Paradiso et al.) and the N and G proteins of RSV; VP4 (previously known as VP3); VP6 and VP7 polypeptides of rotavirus; envelope glycoproteins of HIV; and the surface and presurface antigens of hepatitis B and herpes glycoproteins B and D.

Fungal antigen that can be those derived from fungi including but not limited to Candida spp. (e.g., albicans), Cryptococcus spp. (e.g., neoformans), Blastomyces spp. (e.g., dermatitidis), Histoplasma spp. (e.g., capsulatum), Coccidroides spp. e.g., immitis), Paracoccidroides spp. (e.g., brasiliensis) and Aspergillus spp. Examples of parasite antigens include, but are not limited to, Plasmodium spp., Eimeria spp., Schistosoma spp., Trypanosoma spp., Babesia spp., Leishmania spp., Cryptosporidia spp., Toxoplasma spp. and Pneumocystis spp.

Also of interest are various antigens associated with auto-immune diseases, such as rheumatoid arthritis and lupus erythematosus.

Other applications may also include the elicitation of an immune response to stimulate or inhibit the stability or interaction of cellular modifiers, including hormones with their corresponding receptors or binding components. In this fashion, the immune response can be used to inhibit/enhance growth, reproduction, differentiation, and overall performance.

It is to be understood from the above discussion, that the use of the term antigen is meant to imply either the whole antigen or one of its determinants. The foregoing list of antigens is for exemplary purposes only. Additional antigens which can be used in the antigen-adjuvant compositions of the present invention are readily ascertained by one skilled in the art. Further, the antigen-adjuvant formulations of the present invention are stable for a period of time sufficient to allow the manufacture, shipment and storage of the vaccine formulations.

The following Examples have been included to illustrate preferred modes of the invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

EXAMPLES

Example 1
IL-1α and IL-1β As Mucosal Adjuvants

Materials and Methods

Animals. Female BALB/c and C57BL/6 mice, 16–18 grams, were purchased from Frederick Cancer Research and Developmental Center, National Cancer Institute, Frederick, Md. Animals were housed in filter top cages and provided food and water ad libitum. All procedures for use and care of mice were approved by Duke University's Institutional Animal Care and Use Committee.

Immunization. Mice were intranasally immunized as previously described, Staats et al., *J Immunol* 157:462 (1996); Porgador et al., *J Immunol* 158:834 (1997); Staats et al., *AIDS Research & Human Retroviruses* 13:945 (1997). Briefly, mice (3–4 mice per group) were intranasally immunized with the indicated concentration (Table 2) of ovalbumin (#A-5503 SIGMA, St. Louis, Mo.) or tetanus toxoid (graciously provided by Dr. John Eldridge, Wyeth-Lederle Vaccines and Pediatrics) and the indicated adjuvant in a total volume of 15 $\mu$l (7.5 $\mu$l/nostril). The mucosal adjuvant cholera toxin was obtained from List Biological Laboratories, Inc. (Campbell, Calif.). Recombinant human IL-1α and IL-1β was obtained from the National Cancer Institute Biological Resources Branch, Division of Cancer Treatment, FCRDC (Frederick, Md.). Antigen preparations were diluted to the appropriate concentration in sterile distilled water and 7.5 $\mu$l of the antigen mixture was introduced into each nostril while mice were under isoflurane anesthesia (IsoFlo, USP; SOLVAY Animal Health, Inc., Mendota Heights, Minn.).

Sample collection. Blood was collected from the retroorbital plexus using a heparinized Natelson capillary tube (Baxter Healthcare Corporation, McGaw Park, Ill.) while mice were under isoflurane anesthesia. Vaginal wash samples were collected by washing the vaginal cavity with 100 $\mu$l sterile PBS while mice were anesthetized with isoflurane. This procedure resulted in an approximate ten (10)-fold dilution of vaginal samples, Staats et al., *J Immunol* 157:462 (1996). All samples were stored at −20° C. until assayed for antigen-specific antibodies.

ELISA. Enzyme-linked immunosorbent assay (ELISA) was used to determine the presence of antigen-specific antibodies in serum and vaginal wash samples. The ELISA assay was performed as previously reported, Staats et al., *J Immunol* 157:462 (1996); Staats et al., *AIDS Research & Human Retroviruses* 13:945 (1997), except that ELISA plates were coated with ovalbumin or tetanus toxoid at 5 $\mu$g/ml. The end-point titer represents the reciprocal dilution of the last sample whose optical density is at least two (2)-fold higher than the optical density of a corresponding naive sample. Due to the small vaginal lavage sample sizes, vaginal IgG and IgA responses are reported as end-point ELISA titers instead of standardizing based on total IgG and IgA concentrations, Staats et al., *J Immunol* 157:462 (1996); Staats et al., *AIDS Research & Human Retroviruses* 13:945 (1997).

Cell isolation and proliferation assay. Spleens (SP) were aseptically removed and single cell suspensions were produced by cutting the spleen into small pieces (~5 mm×5 mm) and expressing the cells from the splenic capsule with the sterile end of a 5 cc syringe plunger. Red blood cells were removed by centrifugation over CAPPEL™ Lymphocyte Separation Media (ICN Biomedical, Aurora, Ohio). Cells were adjusted to $2 \times 10^6$ cells/ml in complete T cell media (RPMI 1640, 10% FBS, HEPES, Pen/Strep, 2-ME). To an equal volume of cells was added an equal volume of complete T cell media or media containing 0.2 $\mu$g/ml of the appropriate antigen (ovalbumin or tetanus toxoid) to give a final cell density of $1 \times 10^6$ cells/ml and antigen at 0.1 $\mu$g/ml. Cells (100 ml) were added to round-bottom 96-well microtiter plates in triplicate and incubated in a 37° C., 10% $CO_2$ in air, humidified environment for five days. Four–six (4–6) hours before harvesting, 0.5 $\mu$Ci [$^3$H]-thymidine (NEN Research Products, Boston, Mass.) was added to each well. Cells were harvested onto glass filters using a PHDTM sample harvester (Cambridge Technology Inc., Watertown, Mass.). Incorporation was determined by placing the filters in SCINTIVERSE BDTM scintillation fluid (FISHER, Pittsburgh, Pa.) and counting with a 2000CATRI-CARB@D™ liquid scintillation analyzer (Packard, Downers Grove, Ill.).

Delayed type hypersensitivity (DTH). For the measurement of DTH responses, an ear swelling assay was employed as previously described, Staats et al., *J Immunol* 157:462 (1996); Staats et al., *AIDS Research & Human Retroviruses* 13:945 (1997). Briefly, 25 $\mu$g of immunization antigen was injected into the right ear in 10 $\mu$l sterile PBS while 10 $\mu$l sterile PBS was injected into the left ear as control. Ear swelling was measured 24–48 hours after injection with a dial thickness gauge (Mitutoyo, Japan, code #7326). Antigen-specific ear swelling was calculated by subtracting the ear swelling of the PBS injected ear from the swelling of the antigen-injected ear.

Statistical analysis. Statistical significance was determined using ANOVA™ with comparison of multiple means using Bonferroni (Dunn) T tests, Sidak T tests, and Tukey's Studentized Range Test on SAS™ software (SAS Institute, Cary, N.C.). A difference was considered significantly different if two of three tests indicated a significant difference. The level of significance used was 0.05.

Figure 1:
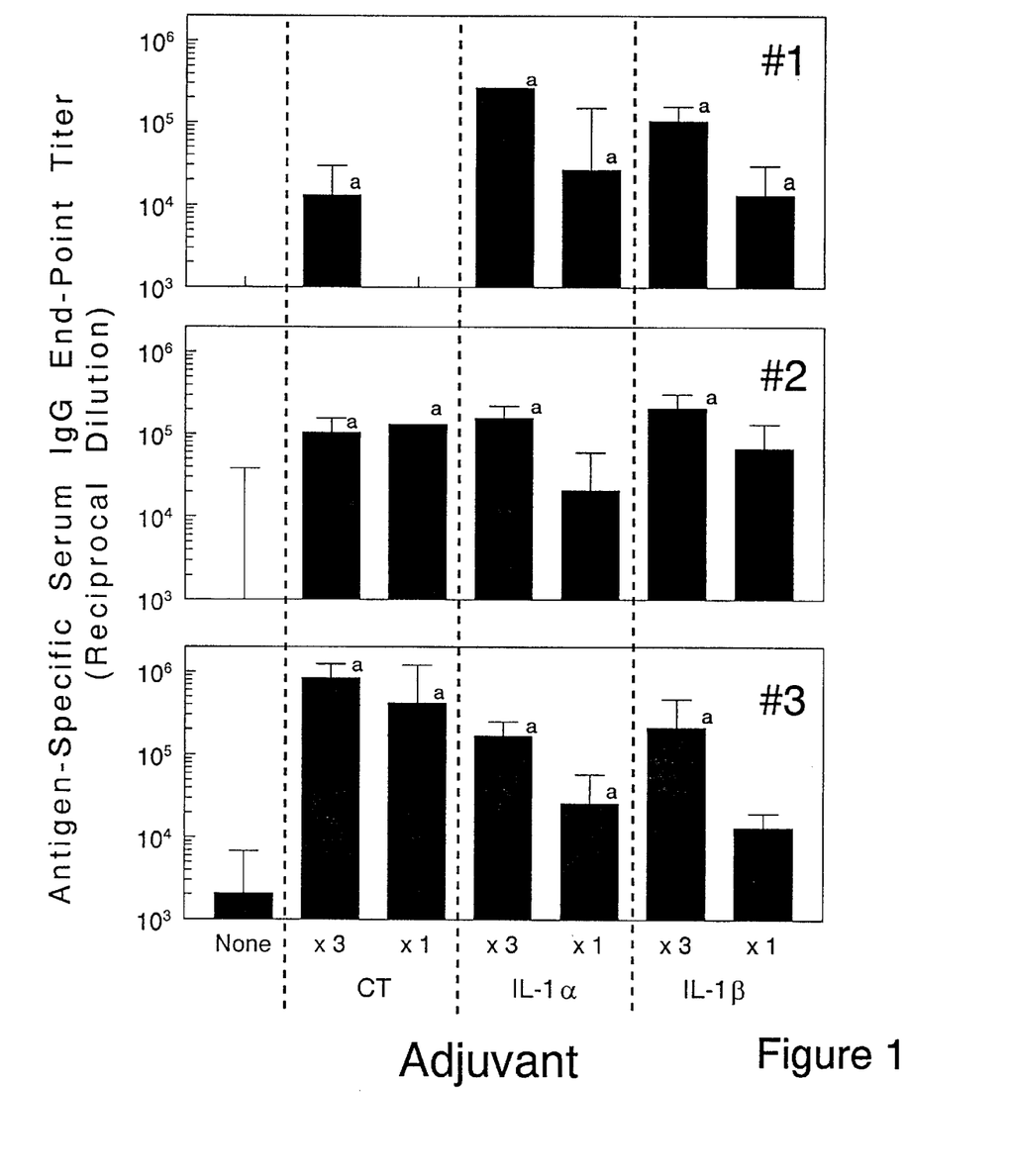
FIG. 1 is a bar graph depicting serum antigen-specific IgG end-point titers (reciprocal) after intranasal immunization as indicated in Table 2. #1=experiment #1; #2 experiment #2; #3=experiment #3. Results for experiment #1 represent day 42 serum. Results for experiments #2 and #3 represent day 21 serum. There were three to four (3–4) mice per group per experiment. a=significantly greater than "none" control ($p<0.05$).

Results. IL-1α and IL-1β enhance serum antigen-specific IgG responses when intranasally administered with soluble protein antigens. To determine if IL-1α or IL-1β possessed mucosal adjuvant activity, BALB/c or C57BL/6 mice were intranasally immunized with antigen alone or antigen in the presence of CT, IL-1α or IL-1β (Table 2). In experiment 1, BALB/c mice were intranasally immunized with 100 μg of ovalbumin on day 0, 14, and 28 in the absence of adjuvants or in the presence of 1 μg of CT, 4 μg IL-1α, or 4 μg IL-1β administered with all immunizations or with the first immunization only (Table 2). Both IL-1α and IL-1β were able to serve as mucosal adjuvants when intranasally administered with ovalbumin with all immunizations (×3) or with the first immunization only (×1) ($p<0.05$ compared to no adjuvant control). When co-administered with all three immunizations, the day 42 serum anti-ovalbumin IgG titer for the IL-1α, IL-1β and CT groups was 1:262,144, 1:104,031 and 1:13,004, respectively (FIG. 1, #1).

IL-1α and IL-1β were also effective adjuvants when administered with the first immunization only. Such administration resulted in serum anti-ovalbumin IgG titers of 1:26,008 and 1:13,004, respectively. Anti-ovalbumin IgG titers were less than 1:100 in the sera collected from mice immunized with no adjuvant or with CT administered with the first immunization only (FIG. 1, #1).

To determine if IL-1α and/or IL-1β exhibited mucosal adjuvant activity when co-administered with a more relevant vaccine antigen, C57BL/6 (Exp. #2) or BALB/c (Exp. #3) mice were intranasally immunized with 50 μg tetanus toxoid (TT) alone or in the presence of adjuvants (Table 2). To comply with other published mucosal immunization protocols, Xu-Amano et al., *Journal of Experimental Medicine*, 178:1309 (1993); Marinaro et al., *J Immunol* 155:4621 (1995), mice were immunized on day 0, 7, and 14 for experiments #2 and #3 (Table 2).

IL-1α and IL-1β were effective mucosal adjuvants when intranasally administered with 50 μg TT on day 0, 7, and 14 in both C57BL/6 (Exp. #2) and BALB/c (Exp. #3) mice ($p<0.05$ as compared to no adjuvant control). When administered with all three immunizations (×3), day 21 serum anti-TT titers for IL-1α and IL-1β groups were 1:155,872 and 1:208,064 for C57BL/6 mice, respectively, and 1:165,140 and 1:208,064, respectively, for BALB/c mice (FIG. 1, #2 and #3). IL-1α also exhibited significant adjuvant activity when intranasally administered to BALB/c mice with TT on day 0 only ($p<0.05$ as compared to no adjuvant control). Within the same experiment, there were no statistically significant differences between any of the CT, IL-1α or IL-1β adjuvant groups.

Antigen-specific IgG subclass end-point titers were measured to compare the antigen-specific IgG subclass responses induced by IL-1α and IL-1β to those induced by CT. The antigen-specific IgG subclass profiles associated with the use of IL-1α or IL-1β as a mucosal adjuvant were comparable to those induced by the use of CT as a mucosal adjuvant (Table 3).

Figure 2:
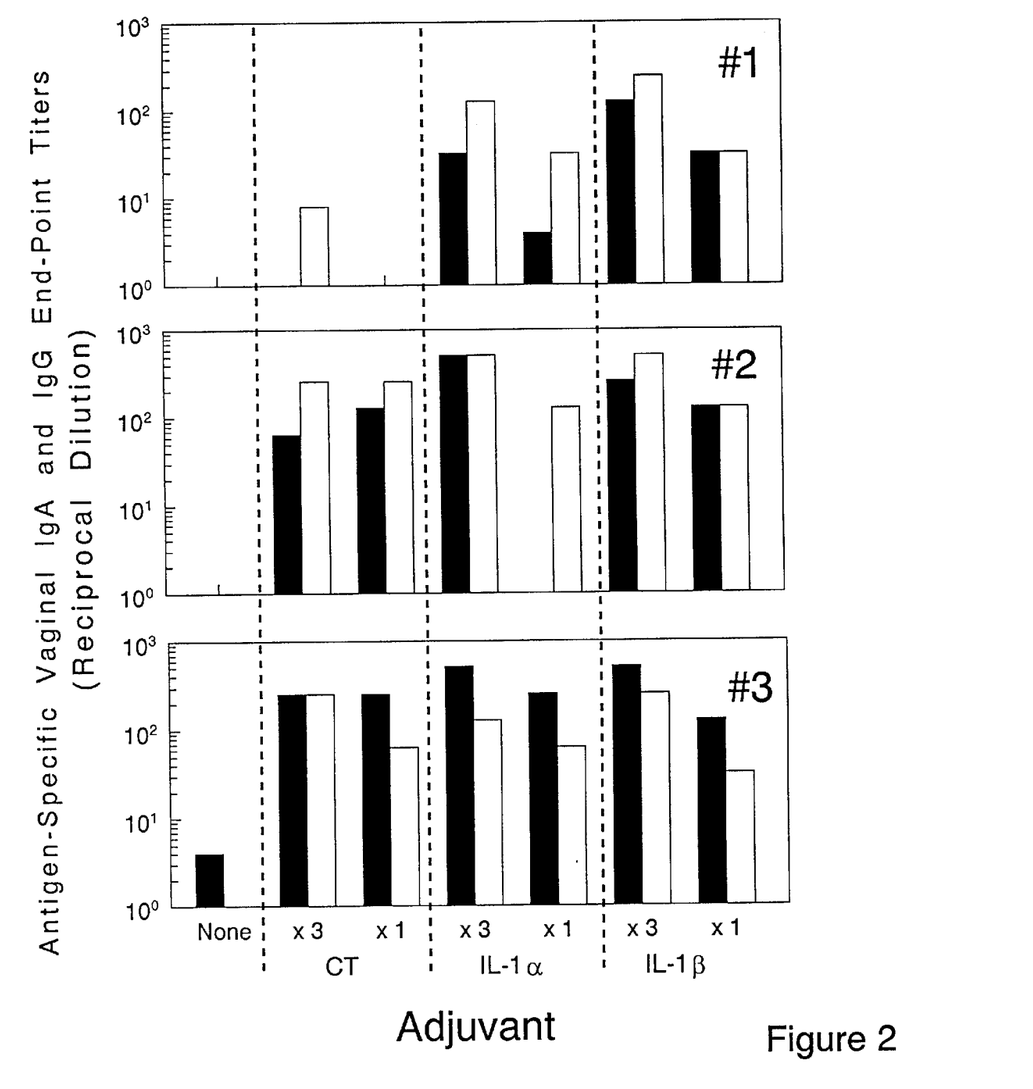
FIG. 2 is a bar graph depicting vaginal antigen-specific IgA end-point titers (reciprocal) after intranasal immunization as indicated in Table 2. There were three to four (3–4) mice per group, per experiment. #1=experiment #1; #2=experiment #2; #3=experiment #3. Results for experiment #1 represent day 42 samples while experiments #2 and #3 represent day 23 vaginal lavage samples. Solid bars=IgA; open bars=IgG. Vaginal lavage samples were pooled for each group.

IL-1α and IL-1β induce mucosal IgA responses when used as a mucosal adjuvant. Vaginal lavage samples were monitored for the presence of antigen-specific IgG and IgA to determine if IL-1α or IL-1β could enhance the production of antigen-specific IgA responses when used as a mucosal vaccine adjuvant. In all experiments, IL-1α and IL-1β were as effective as CT for their ability to induce the production of antigen-specific mucosal IgA and IgG responses (FIG. 2). In experiment #1, when the adjuvants were used with all three immunizations, the day 42 vaginal anti-ovalbumin IgA titers for the IL-1α and IL-1β groups were 1:32 and 1:128, respectively, compared to an undetectable anti-ovalbumin IgA response in the CT group (FIG. 2, #1). Even when used with the first immunization only, IL-1α and IL-1β induced anti-ovalbumin IgA responses that were detectable in vaginal lavage samples (FIG. 2, #1). In experiments #2 and #3, the use of IL-1α and IL-1β with all immunizations (×3) consistently induced antigen-specific vaginal IgA titers that were two to eight (2–8)-fold higher than those induced by CT (FIG. 2, #2 and #3). When administered with TT for the first immunization only, IL-1α (Exp. #3) and IL-1β (Exp. #2 and #3) induced the production of anti-TT vaginal IgA responses.

Figure 3:
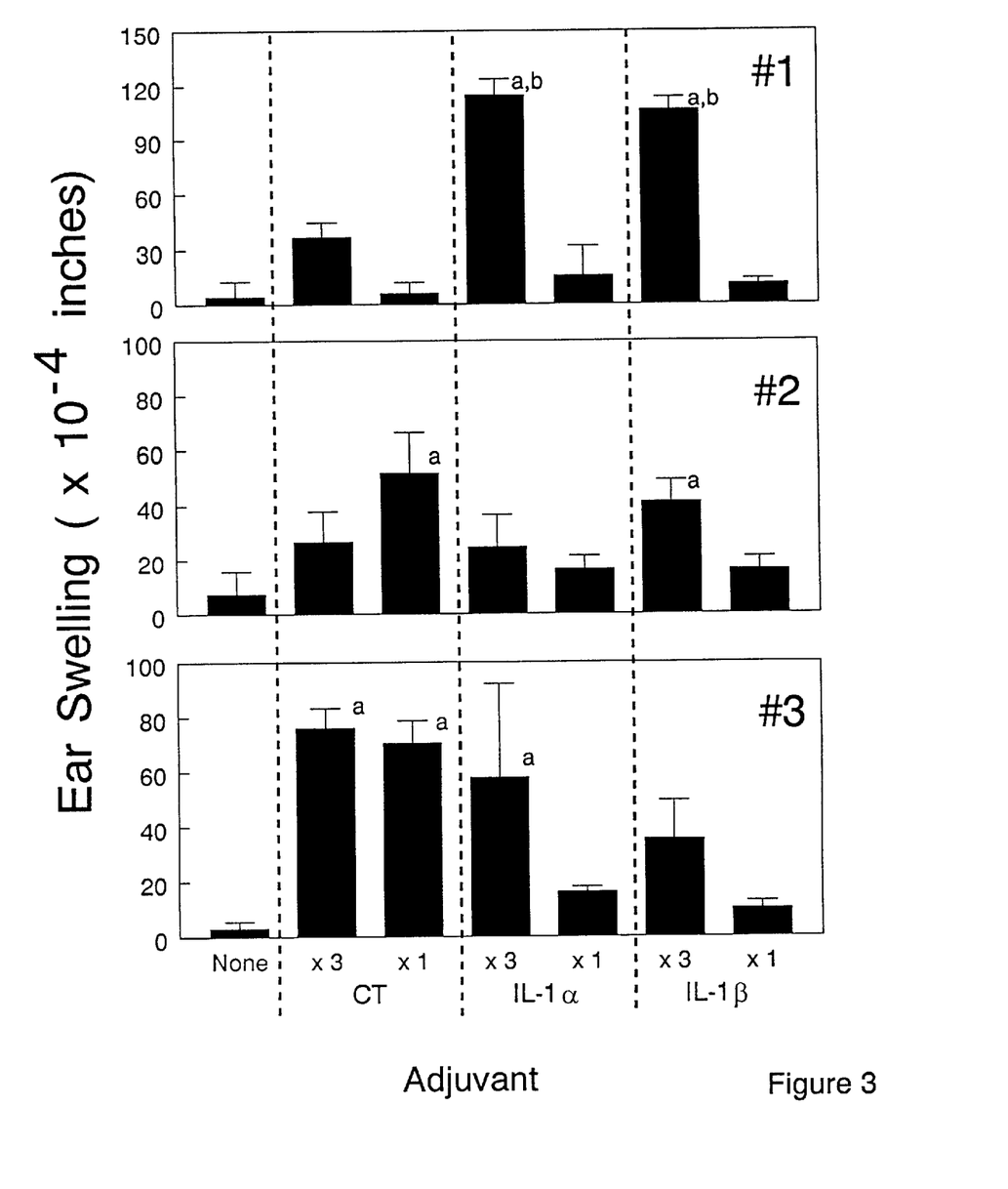
FIG. 3 is a bar graph depicting antigen-specific DTH ear swelling responses after intranasal immunization as indicated in Table 2. There were three to four (3–4) mice per group, per experiment. #1=experiment #1; #2=experiment #2; #3=experiment #3. Results for experiment #1, #2, and #3 represent day 43, 49 and 35 ear swelling responses respectively. a=significantly greater than "none" control ($p<0.05$). b=significantly greater than none, CT×3, CT×1, IL-1α×1, and IL-1β1 groups.
Figure 4:
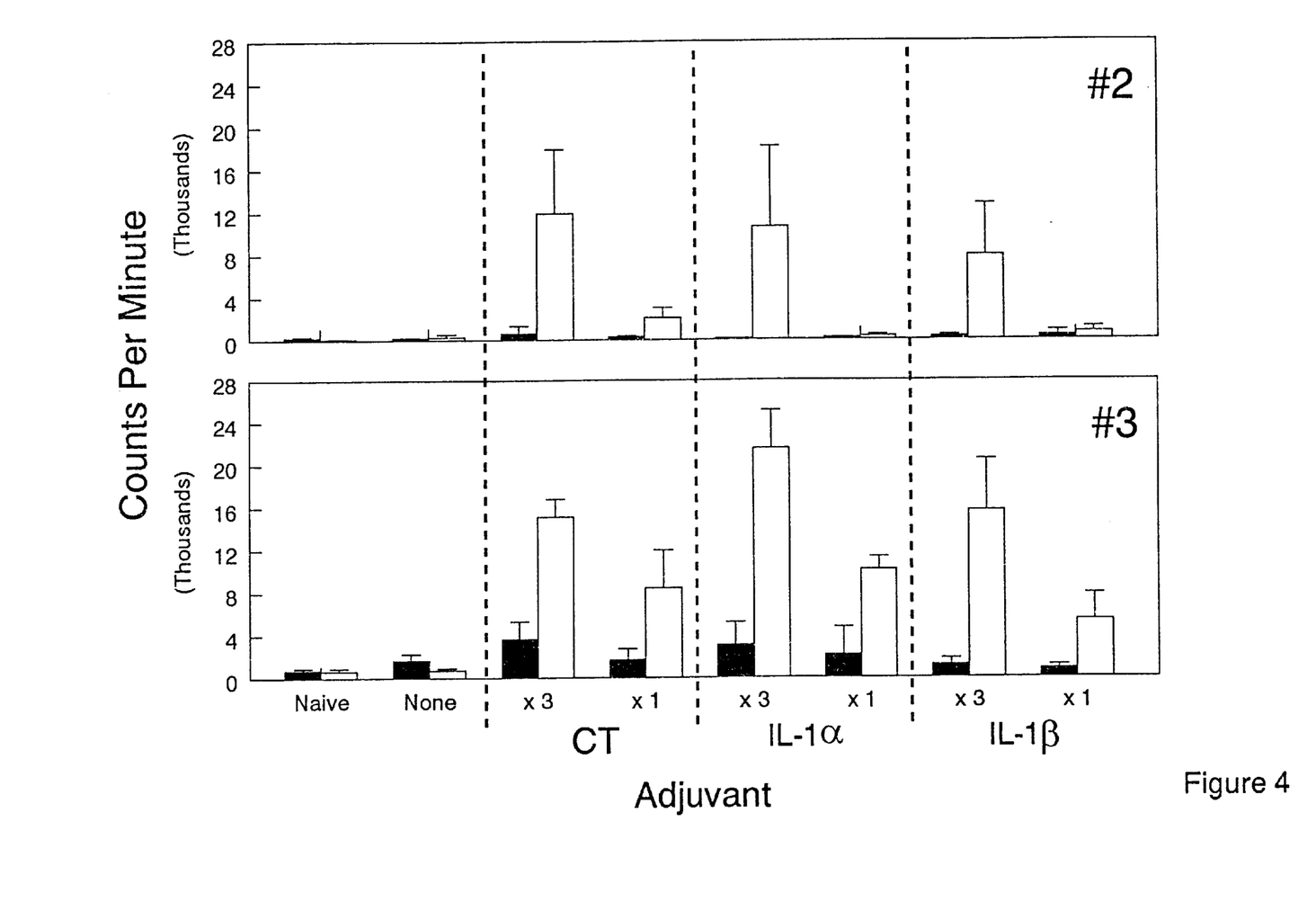
FIG. 4 is a bar graph depicting antigen-specific lymphocyte proliferative responses in splenocytes from animals immunized as indicated in Table 2. Splenocytes were harvested on day 56 for experiments #2 and #3. Solid boxes represent counts per minute for splenocytes cultured in culture media only while the open boxes represent counts per minute for splenocytes cultured in the presence of tetanus toxoid at 0.1 μg/ml. Splenocytes from three to four (3–4) mice were pooled per group.

IL-1α and IL-1β induce cell-mediated immune responses when used as a mucosal adjuvant. Ear-swelling delayed-type hypersensitivity (DTH) responses were used as in indicator of in vivo cell-mediated immune responses after intranasal immunization with soluble protein antigens alone or in the presence of CT, IL-1α or IL-1β. When intranasally administered with ovalbumin for all three immunizations (Exp. #1), IL-1α and IL-1β induced DTH ear-swelling responses (114+8.9, 106+7.6 DTH units, respectively) that were significantly greater than those induced by any other groups ($p<0.05$, FIG. 3). In subsequent studies, IL-1α (×3, Exp. #3) and IL-1β (×3, Exp. #2) induced DTH ear-swelling responses that were significantly greater than those induced by immunization in the absence of adjuvant ($p<0.05$) and comparable to those induced by CT. The use of IL-1 with the first immunization only did not induce significantly elevated DTH ear-swelling responses. Antigen-induced lymphocyte proliferative responses were also monitored as an indicator of antigen-specific, cell-mediated immune responses. Both IL-1α and IL-1β induced lymphocyte proliferative responses comparable to those induced by CT in all three experiments (FIG. 4).

Discussion. Results from this Example indicate that IL-1α and IL-1β are able to serve as mucosal adjuvants when intranasally administered with soluble protein antigens. IL-1α and IL-1β were as effective as CT for the induction of antigen-specific serum IgG, vaginal IgA, as well as in vivo and in vitro cell-mediated immune responses. Although numerous reports have indicated that IL-1 is able to serve as an adjuvant for the induction of antigen-specific immune responses (See e.g., Lin et al., *Clinical Infectious Diseases* 21:1439 (1995); Hakim et al., *Journal of Immunology* 157:5503 (1996)), the present invention provides the first demonstration of mucosal adjuvant activity for IL-1 when intranasally administered with soluble protein antigens.

IL-1α and IL-1β are proinflammatory cytokines produced by many cell types including macrophages, PBMC, fibroblasts, and intestinal epithelial cell lines. (See e.g., Bromander et al., *Journal of Immunology* 146:2908 (1991); Bromander et al., *Scandinavian Journal of Immunology* 37:452 (1993); Dinarello, C. A., *Blood* 87:2095 (1996); Dinarello, C. A., *Faseb J* 8:1314 (1994); Dinarello, C. A., *Chemical Immunology* 51:1 (1992); Krakauer, T., *Cellular Immunology* 172:224 (1996).) IL-1α and IL-1β utilize the same cell-surface receptors, type I and type II, although only the type I IL-1 receptor transduces a signal in response to ligation of the receptor with IL-1. (See e.g., Dinarello, C. A., *Blood* 87:2095 (1996); O'Neill, L. A. J., *Biochimica et Biophysica Acta* 1266:31 (1995); Bankers-Fulbright et al., *Life Sciences* 59:61(1996).) IL-1 induces the gene expression of itself as well as a large number of other proteins including IL-2, IL-3, IL-4, IL-5, IL-6, IL-7, IL-8, IL-12, TGF-β3, TNFα, TNFβ, GM-CSF, G-CSF, M-CSF, and the IL-2 receptor. (See e.g., Dinarello, C. A., *Blood* 87:2095 (1996); Krakauer, T., *Cellular Immunology* 172:224(1996).)

Because of its ability to induce the production of cytokines involved in the induction of immune responses, the potential of IL-1 as a vaccine adjuvant is apparent. However, IL-1 has been extensively studied in humans and found to be extremely toxic after intravenous administration. (See e.g., Dinarello, C. A., *Chemical Immunology* 51:1 (1992); Rinehart et al., *Cancer Investigation* 15:403 (1997); Verschraegen et al., *European Journal of Cancer*, 32A:1609(1996).) With both IL-1α and IL-1β, the predominant side effect observed was fever, chills, hypotension and nausea. In such studies, IL-1 was administered by the intravenous (IV) route and was administered daily for 4 to 14 days.

In sharp contrast, in the methods of the present invention, no toxic side effects (ruffled fur, weight loss) were observed at any time. Additionally, IL-1α and IL-1β were administered locally and were effective adjuvants when administered at weekly (Exp. #2, #3) or biweekly intervals (Exp. #1). In some cases, IL-1 was an effective adjuvant when administered with only the first immunization in a series of immunizations. Because IL-1 stimulation of mucosal epithelial cells down-regulates expression of the type I IL-1 receptor, the inflammatory activity of IL-1 used as a mucosal adjuvant is minimized. (See e.g., McGee et al., *Cellular Immunology* 168:276(1996).)

IL-1α and IL-1β are superior to CT and related molecules as mucosal adjuvants because they are "self" proteins. Although CT is a potent mucosal adjuvant, the fact that it is very immunogenic, in addition to being toxic, diminishes its effectiveness when repeatedly used as a mucosal adjuvant. Indeed, pre-existing immunity to CT reduces its effectiveness as a mucosal adjuvant. (See e.g., Lyce et al., *Scand J Immunol* 33:691 (1991); Wu et al., *Vaccine* 12:215 (1994).) Despite having reduced toxicity in the presence of adjuvant activity, mutant CT molecules maintain their immunogenicity, which also prevents them from being repeatedly used as mucosal adjuvants in humans. (See e.g., Douce et al., *Infection & Immunity* 65:2821 (1997); Fontana et al., *Infection & Immunity* 63:2356 (1995); de Haan et al., *Infection and Immunity* 64:5413 (1996).)

In contrast to CT, IL-1α and IL-1β are "self" proteins and therefore substantially non-immunogenic. Stated differently, IL-1α and IL-1β are substantially less immunogenic than CT and mutant CT adjuvants. Since species-specific cytokines are used as adjuvants, the host will not recognize the cytokine as a foreign substance. Therefore, the host will not mount an immune response against the cytokine and "pre-existing" immunity does not become a problem. Thus, the cytokines may be used repeated without the concern that "anti-cytokine" antibodies will neutralize their adjuvant activity and reduce their effectiveness as mucosal adjuvants.

The correlates of protective immunity for mucosally transmitted HIV are not known. However, both HIV-specific CTL and mucosal IgA appear to be important. (See e.g., Mazzoli et al., *Nature Medicine* 3:1250 (1997); De Maria et al., *Journal of Infectious Diseases* 170:1296(1994).) Heretofore, HIV mucosal vaccine studies in humans have been hampered by the absence of safe and effective mucosal vaccine adjuvants. The results observed through the use of the method of the present invention indicate that 1) IL-1α and IL-1β are effective mucosal adjuvants for the induction of systemic and mucosal immune responses and 2) cytokines are biologically active when intranasally administered. The use of cytokines as mucosal adjuvants is thus useful for the induction of systemic and mucosal immune responses in humans.

TABLE 1

Literature review on the effects of mucosal adjuvants and cytokines on cytokine production and APC acyivity by intestinal epithelial and macrophage cell lines, PBMC, sIgA⁻B cells, and freshly isolated intestinal epithelial cells. APC activity was determined in alloantigen presentation systems.

| Cell Line (type) | Stimulus | IL-1 | IL-6 | IL-8 | IgA Production | APC Activity | Reference |
|---|---|---|---|---|---|---|---|
| IEC-6 (epithelial) | CT | | ↑ | | | | McGee et al. (1993) |
| | CT-B | | ←→ | | | | |
| | IL-1β | | ↑↑ | | | | |
| | TGF-β1 | | ↑ | | | | |
| | TNFα | | ↑↑ | | | | |
| | TGF-β1 + IL-1β | | ↑↑↑ | | | | |
| | TNFα + IL-Iβ + TGF-β1 | | ↑↑↑ | | | | |
| | CT + IL-1β | | ↑↑↑ | | | | |
| | CT + TNF-α | | ↑↑↑ | | | | |
| IEC-17 (epithelial) | CT | ↑↑ | ↑ | | | | Bromander et al. (1993) |
| Caco-2 (epithelial) | IL-1β | | ↑↑↑ | ↑↑ | | | Parikh et al. (1997) |
| HT-29 (epithelial) | IL-1β | | | ↑↑ | | | Eckmann et al. (1993) |
| P388D1 (MF) | CT | ↑↑ | | | | ↑ | Bromander et al., (1991) |
| | CT + anti-IL-1α | ←→ | | | | ←→ | |
| PBMC | CT | ↑↑↑ | ↑↑ | ←→ | | | Krakauer, T. (1996) |
| SlgA⁻ B cells | CT | | | | ↑ | | Kin et al., (1998) |
| | CT + anti-TGF-β | | | | ←→ | | |
| | TGF-β1 | | | | ↑↑ | | |
| | TGF-β1 + anti-TGF-β | | | | ←→ | | |

TABLE 1-continued

Literature review on the effects of mucosal adjuvants and cytokines on cytokine production and APC acyivity by intestinal epithelial and macrophage cell lines, PBMC, sIgA⁻B cells, and freshly isolated intestinal epithelial cells. APC activity was determined in alloantigen presentation systems.

| Cell Line (type) | Stimulus | IL-1 | IL-6 | IL-8 | IgA Production | APC Activity | Reference |
|---|---|---|---|---|---|---|---|
| Freshly Isolated IEC | IL-1β IFN-δ TNF-α | | ↑<br>←→<br>←→ | | | | Panja et al. (1995) |

Symbol legend:
←→ = no change over unstimulated control cells;
↑ = 2–10 fold enhancement over unstimulated controls;
↑ ↑ = 10–100 fold enhancement over unstimulated controls;
↑ ↑ ↑ = >100 fold enhancement over unstimulated controls.

TABLE 2

Immunization protocols to evaluate the mucosal adjuvant activity of IL-1α and IL-1β. There were three to four (3–4) mice per group, per experiment. For technical details concerning the immunization, please see Materials and Methods.

| Groups | Immunogen | Immunization Schedule | Adjuvant | Adjuvant Schedule |
|---|---|---|---|---|
| Exp. #1 (BALB/c) | | | | |
| None | Ovalbumin (100 μg) | Day 0, 14, 28 | None | None |
| CT × 3 | Ovalbumin (100 μg) | Day 0, 14, 28 | CT (1 μg) | Day 0, 14, 28 |
| CT × 1 | Ovalbumin (100 μg) | Day 0, 14, 28 | CT (1 μg) | Day 0 |
| IL-1α × 3 IL-1α × 1 IL-1β × 3 IL-1β × 1 | Ovalbumin (100 μg) | Day 0, 14, 28 | IL-1α (4 μg) | Day 0, 14, 28 |
| | Ovalbumin (100 μg) | Day 0, 14, 28 | IL-1α (4 μg) | Day 0 |
| | Ovalbumin (100 μg) | Day 0, 14, 28 | IL-1β (4 μg) | Day 0, 14, 28 |
| | Ovalbumin (100 μg) | Day 0, 14, 28 | IL-1β (4 μg) | Day 0 |
| Exp. #2 (BALB/c) Exp. #3 (C57BL/6) | | | | |
| None | Tetanus toxoid (50 μg) | Day 0, 7, 14 | None | None |
| CT × 3 | Tetanus toxoid (50 μg) | Day 0, 7, 14 | CT (1 μg) | Day 0, 7, 14 |
| CT × 1 | Tetanus toxoid (50 μg) | Day 0, 7, 14 | CT (1 μg) | Day 0 |
| IL-1α × 3 | Tetanus toxoid (50 μg) | Day 0, 7, 14 | IL-1α (4 μg) | Day 0, 7, 14 |
| IL-1α × 1 | Tetanus toxoid (50 μg) | Day 0, 7, 14 | IL-1α (4 μg) | Day 0 |
| IL-1β × 3 | Tetanus toxoid (50 μg) | Day 0, 7, 14 | IL-1β (4 μg) | Day 0, 7, 14 |
| IL-1β × 1 | Tetanus toxoid (50 μg) | Day 0, 7, 14 | IL-1β (4 μg) | Day 0 |

TABLE 3

Antigen-specific serum IgG subclass profiles after intranasal immunization as described in Materials and Methods and Table 2. Experiment #1 represent day 35 responses, while results for Experiments #2 and #3 represent day 21 responses. Sera from three to four (3–4) mice per group, per experiment was pooled and assayed for antigen-specific IgG1, IgG2a, IgG2b, or IgG3 end-point titers.

| Group | Antigen-Specific End-Point Titer | | | |
|---|---|---|---|---|
| | IgG1 | IgG2a | IgG2b | IgG3 |
| Experiment #1 | | | | |
| None | <64 | <64 | <64 | <64 |
| CT × 3 | 32,768 | <64 | <64 | <64 |
| CT × 1 | <64 | <64 | <64 | <64 |
| IL-1α 3 | 524,288 | 256 | 4,096 | <64 |
| IL-1α 1 | 65,536 | <64 | <64 | <64 |
| IL-1β 3 | 131,072 | 8,182 | 8,192 | <64 |
| IL-1β 1 | 32,768 | <64 | <64 | <64 |
| Experiment #2 | | | | |
| None | 1,024 | <64 | <64 | <64 |
| CT × 3 | 65,536 | 512 | 16,384 | <64 |
| CT × 1 | 65,536 | <64 | 1,024 | <64 |
| IL-1α × 3 | 131,072 | <64 | 8,192 | 512 |
| IL-1α × 1 | 32,768 | <64 | 512 | <64 |
| IL-1β × 3 | 131,072 | <64 | 8,192 | <64 |
| IL-1β × 1 | 65,536 | <64 | 4,096 | <64 |
| Experiment #3 | | | | |
| None | 8,192 | <64 | 512 | <64 |
| CT × 3 | 262,144 | 4,096 | 8,192 | 256 |
| CT × 1 | 262,144 | 4,096 | 8,192 | <64 |
| IL-1α × 3 | 262,144 | 4,096 | 8,192 | <64 |
| IL-1α × 1 | 131,072 | 1,024 | 8,192 | <64 |
| IL-1β × 3 | 262,144 | 8,192 | 8,192 | <64 |
| IL-1β × 1 | 32,768 | 512 | 2,048 | <64 |

TABLE 4

Ability of IL-1α and IL-1β to serve as mucosal adjuvants when intranasally administered with ovalbumin (Experiment #1) or tetanus toxoid (Experiments #2 and #3)

| Exp | Adjuvant | Serum Antigen-Specific IgG Responses | | | Vaginal Antigen-Specific IgA Responses | | | Antigen-Specific Splenocyte Proliferative Responses | | |
|---|---|---|---|---|---|---|---|---|---|---|
| | | IgG Titer | Fold Increase over "No" adjuvant | Fold Increase over "CT" adjuvant | IgA Titer | Fold Increase over "No" adjuvant | Fold Increase over "CT" adjuvant | Lymphocyte Proliferative Responses at 0.1 μg/ml antigen | Fold Increase over "No" adjuvant | Fold Increase over "CT" adjuvant |
| #1 | None | <1:64 | | | <1:4 | | | Not determined. | | |
| | CT × 3 | 1:13,004 | >203 | | <1:4 | None | | | | |
| | IL-1α × 1 | 1:26,008 | >406 | 2 | 1:4 | >1 | >1 | | | |
| | IL-1α × 3 | 1:262,144 | >4,096 | 20 | 1:32 | >8 | >8 | | | |
| | IL-1β × 1 | 1:23,004 | >203 | None | 1:32 | >8 | >8 | | | |
| | IL-1β × 3 | 1:104,032 | >1,625 | 8 | 1:128 | >32 | >32 | | | |
| #2 | None | 1:256 | | | <1:4 | | | 310 | | |
| | CT × 3 | 1:104,032 | 406 | | 1:64 | >16 | | 11908 | | |
| | IL-1α × 1 | 1:20,643 | 80 | None | <1:4 | None | None | 338 | | |
| | IL-1α × 3 | 1:155,872 | 608 | 1.49 | 1:512 | >128 | 8 | 10638 | | |
| | IL-1β × 1 | 1:65,536 | 256 | None | 1:128 | >32 | 2 | 704 | | |
| | IL-1β × 3 | 1:208,064 | 812 | 2 | 1:256 | >64 | 4 | 7931 | | |
| #3 | None | 1:2,048 | | | 1:4 | | | 757 | | |
| | CT × 3 | 1:832,255 | 406 | None | 1:256 | 64 | | 15108 | 20 | |
| | IL-1α × 1 | 1:26,008 | 12 | None | 1:256 | 64 | None | 10140 | 13 | None |
| | IL-1α × 3 | 1:165,140 | 80 | None | 1:512 | 128 | 2 | 21556 | 28 | 1.4 |
| | IL-1β × 1 | 1:13,004 | 6 | None | 1:128 | 32 | None | 5414 | 7 | None |
| | IL-1β × 3 | 1:208,064 | 101 | None | 1:512 | 128 | 2 | 15671 | 20 | None |

In Table 4, IgG and IgA titers represent the final dilution of sample (serum or vaginal lavage, respectively) that gives a positive response in an antigen-specific ELISA assay. Lymphocyte proliferative responses represent "counts per minute" of splenocytes stimulated in vitro with 0.1 μg/ml of immunizing antigen and cultured for 5 days.

For each category (serum IgG, vaginal IgA, or splenocyte proliferative responses), fold increase over no adjuvant was calculated by dividing the response induced in the presence of adjuvant by the response induced in the absence of adjuvant. To calculate fold increase over CT positive control, the response induced in the presence of IL-1α or IL-1β was divided by the response induced when using CT as a positive control.

In Table 4, mice were immunized on day 0, 14, and 28 with 100 μg ovalbumin for Experiment #1 and on day 0, 7, and 14 with 50 μg tetanus toxoid for Experiments #2 and #3. CT was employed as a positive control mucosal adjuvant and was administered with each immunization (×3) at a dose of 1 μg. IL-1α and IL-1β were tested as mucosal adjuvants at a dose of 4 μg. IL-1α or IL-1β was administered with the first immunization only (×1) or with all three immunizations (×3).

Table 4 indicates that both IL-1α and IL-1β exhibit mucosal adjuvant activity when intranasally administered with soluble protein antigens as determined by their ability to enhance the induction of antigen-specific serum IgG, vaginal IgA, and splenocyte proliferative responses (as compared to responses induced in the absence of adjuvants). In some cases, IL-1α and IL-1β induced antigen-specific responses that were superior to those induced by the positive control adjuvant, CT.

Example 2
Synthetic IL-1β Peptide as a Mucosal Adjuvant

Recombinant interleukin 1β and the synthetic IL-1β peptide 163-171 each possess mucosal adjuvant activity in accordance with the methods of the present invention. In this Example, BALB/c female mice were purchased from Charles River Laboratories and divided into groups of three to four (3–4) mice per group. All mice were intranasally immunized with 100 μg ovalbumin in distilled water in a total volume of 15 μL (7.5 μL per nostril). A total of five groups was used to test the adjuvant activity of IL-1α, IL-1β, and the IL-1β peptide as compared to the adjuvant activity of cholera toxin (Table 4). Mice were immunized a total of three times a week at two week intervals (day 0, day 14, and day 28). Serum was collected at day 35 and assayed for the presence of anti-ovalbumin IgG with ELISA, as described above. DTH responses were measured on day 42 by injecting 10 μL of sterile PBS into the left ear pinna and 10 μL of sterile PBS containing 30 μg ovalbumin into the right ear. Ear-swelling was measured 24 hours later; antigen-specific DTH responses were calculated by subtracting the PBS (left) ear-swelling from the ovalbumin (right) ear-swelling. Ear-swelling units correspond to $1 \times 10^{-4}$ inches.

TABLE 5

| Ovalbumin (μg) | Adjuvant (μg) | Peak Serum anti-ovalbumin serum IgG titer | Anti-ovalbumin DTH response |
|---|---|---|---|
| 100 | none | <1:100 | 4.24 ± 8.5 |
| 100 | cholera toxin (1) | 1:3,250 | 36.7 ± 8.1 |
| 100 | IL-1α (4) | 1:131,072 | 114.7 ± 8.9 |
| 100 | IL-1β (4) | 1:65,536 | 106 ± 7.6 |
| 100 | IL-1β peptide (225) | 1:2,580 | 16 ± 1.4 |

For this Example, IL-1α and IL-1β were effective when intranasally administered with antigen at dosages of 200 μg/kg (high dose) and 67 μg/kg (low dose). The 163-171 IL-1β peptide was used at dosages of 11.25 mg/kg.

Example 3
Use of IL-15 and GM-CSF as Mucosal Adjuvants.

In accordance with the methods of the present invention, IL-15 or GM-CSF were admixed with 100 μg C4-V4 Roman IIIB HIV peptide vaccine (contains T-helper, V-cell and CTL epitopes) and delivered intranasally to BALB/c mice on day 0, 7, 14, and 21. Control mice received peptide only (negative control) or peptide and cholera toxin (positive control). Serum was collected on day 28 and tested for the presence of anti-C4-V3 IIIB IgG. Both IL-15 and GM-CSF served as mucosal adjuvants as indicated by the detection of antigen-specific serum IgG responses of 1:16,384 for both IL-15 and GM-CSF groups as compared to undetectable serum IgG responses in the negative control group and titer of 1:41,285 in the positive control group.

To determine if IL-15 or GM-CSF could enhance the immune response induced by intranasal immunization with peptide and CT, mice were immunized with peptide, CT and IL-15; or peptide, CT, and GM-CSF. The combination of CT and GM-CSF was not superior to GM-CSF alone or CT alone. However, the combination of CT and IL-15 induced a serum anti-peptide IgG titer ten (10)-fold better than that induced by IL-15 alone and four (4) times higher than that induced by peptide and CT.

These results indicate that 1) IL-15 and GM-CSF are active when delivered intranasally and 2) IL-15 and GM-CSF exhibit mucosal adjuvant activity when intranasally delivered with peptide vaccines.

Immunization Schedule: 100 μg C4-V3 IIIB intranasally to BALB/c mice on day 0, 7, 14, and 21 alone or with:

| CT (1 μg) | | CT and IL-15 (1 μg each) |
|---|---|---|
| IL-15 (1 μg) | OR | |
| GM-CSF (1 μg) | | CT and GM-CSF (1 μg each) |

TABLE 6

Mucosal Adjuvant Activity of IL-15 and GM-CSF
Intranasally Administered with C4-V3 IIIB HIV Peptide

| Immunization Group | Serum IgG End-point Titer (reciprocal) |
|---|---|
| C4-V3 IIIB | <100 |
| C4-V3 IIIB + CT | 41,285 |
| C4-V3 IIIB + IL-15 | 16,384 |
| C4-V3 IIIB + CT + IL-15 | 165,140 |
| C4-V3 IIIB + GM-CSF | 16,384 |
| C4-V3 IIIB + CT + GM-CSF | 8,192 |

Example 4

Combinations of Substantially Non-Toxic Biologically Active Adjuvants in Mucosal Immunization As described above, the induction of antigen-specific mucosal immunity is beneficial for the prevention of infections due to pathogenic microorganisms that initiate infection at the mucosal surfaces of the host. Additionally, mucosal immune responses may be beneficial for the treatment of malignant tumors that metastasize to mucosal tissues. To induce mucosal immune responses, antigens are delivered via a mucosal route in accordance with the methods of the present invention. In this Example, the use of cytokines/chemokines/growth factors/apoptosis inhibitors in selected combinations as adjuvants is described for enhancing the induction of antigen-specific systemic and mucosal immune responses when administered along with a vaccine antigen via the intranasal or other mucosal route (e.g., genital, rectal, or oral).

In accordance with the present invention, vaccine-induced immunity is enhanced by the use of biologically active molecules that:

1. Promote angiogenesis at the site of immunization and therefore enhance the blood flow to the site of immunization. Increased blood flow produces an increased number of lymphocytes at the site of immunization that may thus be available to participate in the induction of vaccine-specific immune responses.

2. Promote chemotaxis of dendritic cells and/or subsets of lymphocytes to the site of immunization. Increased numbers of local dendritic cells may thus result in increased antigen presentation and enhanced immunity. Increasing the numbers of specific lymphocyte subsets at the site of immunization skews the immune response towards T-helper type 1 (Th1) or T-helper type 2 (Th2). This mechanism is thus an excellent candidate through which to target vaccines to produce primarily antibody or cellular immune responses.

3. Prevent or inhibit apoptosis of antigen-specific lymphocytes. This leads to an increased number of vaccine-specific lymphocytes and a qualitatively and quantitatively better immune response.

4. Combinations of agents with the above qualities may be used to enhance the effectiveness of agents used individually (Table 7).

TABLE 7

| Group | IL-1 | Cytokine |
|---|---|---|
| 1 | None | None |
| 2 | Yes | None |
| 3 | Yes | IL-5 |
| 4 | Yes | IL-6 |
| 5 | Yes | IL-12 |
| 6 | Yes | IL-15 |
| 7 | Yes | TGFβ |
| 8 | Yes | IFNα |
| 9 | Yes | GM-CSF |
| 10 | Yes | Angiogenic Factor(s) |
| 11 | Yes | Chemotactic Factor(s) |
| 12 | Yes | Apoptosis Inhibitor(s) |
| 13 | | Multiple Combinations |

The adjuvant molecules described in this Example are administered according to the dosage ranges and schedules described above.

Angiogenic factors: Basic fibroblast growth factor, vascular endothelial growth factor, and hyaluronan fragments. Esser et al., *J Cell Biol* 140:947 (1998); Arkonac et al., *J Biol Chem* 273:4400 (1998); Qu et al., *Int Arch Allergy Immunol* 115:47 (1998).

Chemotacticfactors: LARC (Liverand Activation Regulated Chemokine) see e.g., Hieshima et al., *Journal of Biolgocial Chemistry* 272:5846 (1997); PARC (Pulmonary and Activation Regulated Chemokine) see e.g., Hieshima et al., *Journal of Immunology* 159:1140 (1997); MDC (macrophage derived chemokine) see e.g., Godiska et al., *Journal of Experimental Medicine* 185:1595 (1997); TARC (Thymus and Activation Regulated Chemokine) see eg., lmai et al., *Journal of Biological Chemistry* 271:21514 (1996); SLC (Secondary Lymphoid-Tissue Chemokine) see e.g., Nagira et al., *Journal of Biological Chemistry* 272:19518 (1997); Fractalkine (FKN) see e.g., Imai et al., *Cell* 91:521 (1997).

Chemokines that attract dendritic cells to a site of immunization are adjuvant candidates. Immature CCR6+dendritic cells (iDC) which are attracted by LARC (Liver and Activation Regulated Chemokine) are highly phagocytic and uptake antigen well for later presentation to T cells. GM-CSF and other cytokines like TNF induce DC maturation and improved antigen presentation by DC. Thus, LARC alone, or in combination with GM-CSF or other cytokines, is an excellent adjuvant candidate.

Chemokines skew the immune response towards Th1vs. Th2by attracting subsets of T lymphocytes to the site of immunization. MDC (macrophage derived chemokine) and TARC that are highly expressed by dendritic cells and that preferentially attract CCR4+ or CCR8+Th2cells may thus skew the response towards antibody production. Chemokines like SLC (Secondary Lymphoid Organ Chemokine) or fractalkine (FKN) which attract naive T lymphocytes or CD8+ T lymphocytes may thus enhance the CTL response.

Inhibitors of Apoptosis: toso, inhibitors of caspase-8 see e.g., Hitoshi et al., *Immunity* 8:461 (1998).

REFERENCES

The references listed below as well as all references cited in the specification are incorporated herein by reference to the extent that they supplement, explain, provide a background for or teach methodology, techniques and/or compositions employed herein.

Annu. Rev. Immunol. (1995) 13:251–276.
Arkonac et al. (1998) *J Biol Chem* 273:4400.
Bankers-Fulbright et al. (1996) *Life Sciences* 59:61.
Boraschi et al. (1988) *Journal of Experimental Medicine* 168:675.
Bromander et al. (1991) *Journal of Immunology* 146:2908.
Bromander et al. (1993) *Scandinavian Journal of Immunology* 37:452.
Cong et al. (1997) *Journal of Immunology* 159:5301.
de Haan et al. (1996) *Infection and Immunity* 64:5413.
De Maria et al. (1994) *Journal of Infectious Diseases* 170:1296.
Di Tommaso et al. (1996) *Infection & Immunity* 64:974.
Dinarello, C. A. (1992) *Chemical Immunology* 51:1.
Dinarello, C. A. (1996) *Blood* 87:2095.
Dinarello, C. A. (1994) *Faseb J* 8:1314.
Douce et al. (1997) *Infection & Immunity* 65:2821.
Eckmann et al. (1993) *Gastroenterology* 105:1689.
Elson et al. (1984) *J Immunol* 132:2736.
Elson et al. (1984) *J Immunol* 133:2892.
Elson et al. (1987) *Adv Exp Med Biol* 216B:877.
Elson et al. (1994) "Mucosal Adjuvants", In *Handbook of Mucosal Immunology*. eds. Academic Press, Inc., San Diego, p. 391.
Elson, C. O. (1996) "Cholera toxin as a mucosal adjuvant", In *Mucosal Vaccines*. eds. Academic Press, New York, p. 59.
Esser et al. (1998) *J Cell Biol* 140:947.
Fontana et al. (1995) *Infection & Immunity* 63:2356.
Godiska et al. (1997) *Journal of Experimental Medicine* 185:1595.
Hakim et al. (1996) *Journal of Immunology* 157:5503.
Haynes et al. (1996) *Science* 271:324.
Hieshima et al. (1997) *Journal of Biological Chemistry* 272:5846.
Hieshima et al. (1997) *Journal of Immunology* 159:1140.
Hitoshi et al. (1998) *Immunity* 8:461.
Hoyne et al. (1993) *Journal of Experimental Medicine* 178:1783.
Husby et al. (1994) *Journal of Immunology* 152:4663.
Imai et al. (1997) *Cell* 91:521.
Imai et al. (1996) *Journal of Biological Chemistry* 271:21514.
J. Immunol. (1996) 156:887–894.
J. Immunol. (1998) 160:1742–1749.
Janik et al. (1996) *Journal of the National Cancer Institute* 88:44.
Kim et al. (1998) *Journal of Immunology* 160:1198.
Krakauer, T. (1996) *Cellular Immunology* 172:224.
Levine et al. (1983) *Microbiological Reviews* 47:510.
Lin et al. (1995) *Clincial Infectious Diseases* 21:1439.
Lindner et al. (1994) *Scandanavian Journal of Immunology* 40:564.
Lofthouse et al. (1995) *Vaccine* 13:1277.
Lycke et al. (1991) *Scand J Immunol* 33:691.
Lycke et al. (1986) *Immunology* 59:301.
Marinaro et al. (1995) *J Immunol* 155:4621.
Mascarenhas et al. (1996) *Immunological Investigations* 25:333.
Mazzoli et al. (1997) *Nature Medicine* 3:1250.
McGee et al. (1996) *Cellular Immunology* 168:276.
McGee et al. (1993) *Infection & Immunity* 61:4637.
McGee et al. (1995) *Immunology* 86:6.
McGee et al. (1993) *J Immunol* 151:970.
McGee et al. (1992) *Immunology* 77:7.
Mowat, A. M. (1994) "Oral tolerance and regulation of immunity to dietary antigens", In *Handbook of Mucosal Immunology*. Ogra et al. eds. Academic Press, Inc., San Diego, p. 185.
Nagira et al. (1997) *Journal of Biological Chemistry* 272:19518.
Nemunaitis et al. (1994) *Blood* 83:3473.
Nencioni et al. (1987) *Journal of Immunology* 139:800.
Ogra, P. L. (1996) "Mucosal Immunoprophylaxis: An Introductory Overview", In *Mucosal Vaccines*. Kiyono et al., eds. Academic Press, San Diego, p. 3.
O'Hagan, D. T. (1997) *Journal of Pharmacy and Pharmacology* 49:1.
O'Neill, L. A. J. (1995) *Biochimica et Biophysica Acta* 1266:31.
Panja et al. (1995) *Clin Exp Immunol* 100:298.
Paradiso et al. (1989) WO89/02935.
Parikh et al. (1997) *J Surg Res* 69:139.
Parikh et al. (1997) *Shock* 8:249.
Porgador et al. (1997) *J Immunol* 158:834.
Prakken et al. (1997) *Proc Nat Acad of Sci USA* 94:3284.
Qu et al. (1998) *Int Arch Allergy Immunol* 115:47.
Rinehart et al. (1997) *Cancer Investigation* 15:403.
Roberts et al. (1995) *Infection & Immunity* 63:2100.
Rowland-Jones et al. (1993) *Lancet* 341:860.
Snider et al. (1994) *Journal of Immunology* 153:647.
Spangler, B. D. (1992) *Microbiological Reviews* 56:622.
Staats et al. (1997) *AIDS Research & Human Retroviruses* 13:945.
Staats et al. (1996) *J Immunol* 157:462.
Staines et al. (1996) *Clinical & Experimental Immunology* 103:368.
Staruch et al. (1983) *Journal of Immunology* 130:2191.
Sutherland et al. (1994) *Am J Physiol* 266:C1198.
Tagliabue et al. (1993) *Vaccine* 11:594.
Varilek et al. (1994) *Am J Physiol* 267:G1101.
Veltri et al. (1996) *Stem Cells* 14:164.
Verschraegen et al. (1996) *European Journal of Cancer* 32A:1609.
Weisdorf et al. (1 994) *Blood* 84:2044.
Wilson et al. (1993) *Vaccine* 11:113.
Wu et al. (1994) *Vaccine* 12:215.
Xiao et al. (1997) *Clin Immunol Immunopathol* 85:119.
Xu-Amano et al. (1993) *Journal of Experimental Medicine* 178:1309.
Yamamoto et al. (1997)*Proc Nat Acad of Sci USA* 94:5267.

Yamamoto et al. (1997) *Journal of Experimental Medicine* 185:1203.

Zhu et al. (1998) *Journal of Neuropathology & Experimental Neurology* 57:291.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of eliciting an immune response against an antigen in a vertebrate subject, the method comprising the steps of:
   (a) providing an antigen-adjuvant composition comprising the antigen and a substantially nontoxic cytokine adjuvant molecule having biological activity in mucosal tissues and having less immunogenicity than cholera toxin, wherein the antigen-adjuvant composition is soluble in water, and wherein the cytokine adjuvant molecule is selected from the group consisting of an IL, GM-CSF, and combinations thereof; and
   (b) administering said antigen-adjuvant composition intramucosally to the vertebrate subject in a manner such that initial contact occurs in mucosal tissue of the vertebrate subject, whereby an immune response is elicited, the immune response comprising a systemic immune response.

2. The method of claim 1, wherein the antigen-adjuvant composition further comprises a pharmaceutically acceptable vehicle and the antigen-adjuvant composition is carried therein.

3. The method of claim 2, wherein the pharmaceutically acceptable vehicle is selected from the group consisting of distilled water and phosphate-buffered saline.

4. The method of claim 1, wherein the antigen-adjuvant composition is free of mineral adjuvants, preservatives and stabilizers, wherein the antigen-adjuvant composition is soluble in water, and wherein the antigen and adjuvant are not conjugated together.

5. The method of claim 1, wherein the adjuvant is selected from the group consisting of cytokines, chemokines, growth factors, angiogenic factors, apoptosis inhibitors, hormones, and combinations thereof.

6. The method of claim 1, wherein the IL is selected from the group consisting of IL-1, IL-1α, IL-1β, IL-2, IL-5, IL-6, IL-12, IL-15, IL-18, and combinations thereof.

7. The method of claim 6, wherein the IL comprises IL-1α or IL-1β and the IL-1α or IL-1β adjuvant is present in the antigen-adjuvant composition in an amount ranging from about 10 to about 1000 micrograms per kilogram body weight of the vertebrate subject.

8. The method of claim 7, wherein the IL-1α or IL-1β adjuvant is present in the antigen-adjuvant composition in an amount ranging from about 50 to about 500 micrograms per kilogram body weight of the vertebrate subject.

9. The method of claim 8, wherein the IL-1α or IL-1β adjuvant is present in the antigen-adjuvant composition in an amount ranging from about 60 to about 200 micrograms per kilogram body weight of the vertebrate subject.

10. The method of claim 6, wherein the IL comprises recombinant IL-1β and is present in the antigen-adjuvant composition in an amount ranging from about 1 to about 100 milligrams per kilogram body weight of the vertebrate subject.

11. The method of claim 10, wherein the recombinant IL-1β is present in the antigen-adjuvant composition in an amount ranging from about 5 to about 50 milligrams per kilogram body weight of the vertebrate subject.

12. The method of claim 11, wherein the recombinant IL-1β is present in the antigen-adjuvant composition in an amount of about 10 to about 20 milligrams per kilogram body weight of the vertebrate subject.

13. The method of claim 1, wherein said manner of administration is selected from the group consisting of intranasal administration, intravaginal administration, and intrarectal administration.

14. The method of claim 1, wherein the antigen-adjuvant composition is administered once a week over a period of one to three weeks.

15. The method of claim 1, wherein the antigen-adjuvant composition is administered once every two weeks over a period of two to six weeks.

16. The method of claim 1, wherein the antigen-adjuvant composition is administered once during a first week, and the method further comprises the step of administering the antigen only once a week over a period of one to two weeks following the first week.

17. The method of claim 1, wherein the antigen-adjuvant composition is administered once during a first biweekly period, and the method further comprises the step of administering the antigen only once every two weeks over a period of two to four weeks following the first biweekly period.

18. The method of claim 1, wherein the systemic immune response comprises the production of antigen-specific IgG's at a titer of at least about 1:10,000.

19. The method of claim 18, wherein the systemic immune response comprises the production of antigen-specific IgG's at a titer of at least about 1:20,000.

20. The method of claim 1, wherein the immune response further comprises a mucosal immune response.

21. The method of claim 20, wherein the mucosal immune response comprises production of antigen-specific IgA's in mucosal tissue at a site in the vertebrate subject removed from the site of administration.

22. The method of claim 21, wherein the antigen-specific IgA's are produced at a titer of at least about 1:100.

23. The method of claim 22, wherein the antigen-specific IgA's are produced at a titer of at least about 1:500.

24. The method of claim 1, wherein the immune response further comprises a cell-mediated immune response.

25. The method of claim 24, wherein the cell-mediated immune response comprises proliferation of lymphocytes.

26. The method of claim 25, wherein the proliferation of lymphocytes further comprises at least about a ten (10)-fold increase in lymphocytes as compared to an unimmunized state.

27. The method of claim 26, wherein the proliferation of lymphocytes further comprises at least about a fifty (50)-fold increase in lymphocytes as compared to an unimmunized state.

28. The method of claim 1, wherein the vertebrate subject is a mammal.

29. The method of claim 28, wherein the mammal is a human.

30. A method of eliciting an immune response against an antigen in a vertebrate subject, the method comprising the steps of:
   (a) providing an antigen-adjuvant composition comprising the antigen and a cytokine adjuvant molecule having biological activity in mucosal tissues, wherein the antigen-adjuvant composition is free of alum, wherein the antigen-adjuvant composition is soluble in water, wherein the cytokine adjuvant molecule is selected from the group consisting of an IL, GM-CSF and combinations thereof, and wherein the antigen and adjuvant are not conjugated together; and (b) administering said antigen-adjuvant composition intramucosally to the vertebrate subject in a manner such that initial contact occurs in mucosal tissue of the vertebrate subject, whereby an immune response is elicited, the immune response comprising a systemic immune response.

31. The method of claim 30, wherein the antigen-adjuvant composition further comprises a pharmaceutically acceptable vehicle and the antigen-adjuvant composition is carried therein.

32. The method of claim 31, wherein the pharmaceutically acceptable vehicle is selected from the group consisting of distilled water and phosphate-buffered saline.

33. The method of claim 30, wherein the IL is selected from the group consisting of IL-1, IL-1α, IL-1β, IL-2, IL-5, IL-6, IL-12, IL-15, IL-18, and combinations thereof.

34. The method of claim 33, wherein the IL comprises IL-1α or IL-1β and the IL-1α or IL-1β adjuvant is present in the antigen-adjuvant composition in an amount ranging from about 10 to about 1000 micrograms per kilogram body weight of the vertebrate subject.

35. The method of claim 34, wherein the IL-1α or IL-1β adjuvant is present in the antigen-adjuvant composition in an amount ranging from about 50 to about 500 micrograms per kilogram body weight of the vertebrate subject.

36. The method of claim 35, wherein the IL-1α or IL-1β adjuvant is present in the antigen-adjuvant composition in an amount ranging from about 60 to about 200 micrograms per kilogram bodyweight of the vertebrate subject.

37. The method of claim 33, wherein the IL comprises recombinant IL-1β and is present in the antigen-adjuvant composition in an amount ranging from about 1 to about 100 milligrams per kilogram body weight of the vertebrate subject.

38. The method of claim 37, wherein the recombinant IL-1β is present in the antigen-adjuvant composition in an amount ranging from about 5 to about 50 milligrams per kilogram body weight of the vertebrate subject.

39. The method of claim 38, wherein the recombinant IL-1β is present in the antigen-adjuvant composition in an amount of about 10 to about 20 milligrams per kilogram body weight of the vertebrate subject.

40. The method of claim 30, wherein said manner of administration is selected from the group consisting of intranasal administration, intravaginal administration, and intrarectal administration.

41. The method of claim 30, wherein the antigen-adjuvant composition is administered once a week over a period of one to three weeks.

42. The method of claim 30, wherein the antigen-adjuvant composition is administered once every two weeks over a period of two to six weeks.

43. The method of claim 30, wherein the antigen-adjuvant composition is administered once during a first week, and the method further comprises the step of administering the antigen only once a week over a period of one to two weeks following the first week.

44. The method of claim 30, wherein the antigen-adjuvant composition is administered once during a first biweekly period, and the method further comprises the step of administering the antigen only once every two weeks over a period of two to four weeks following the first biweekly period.

45. The method of claim 30, wherein the systemic immune response comprises the production of antigen-specific IgG's at a titer of at least about 1:10,000.

46. The method of claim 45, wherein the systemic immune response comprises the production of antigen-specific IgG's at a titer of at least about 1:20,000.

47. The method of claim 30, wherein the immune response further comprises a mucosal immune response.

48. The method of claim 47, wherein the mucosal immune response comprises production of antigen-specific IgA's in mucosal tissue at a site in the vertebrate subject removed from the site of administration.

49. The method of claim 48, wherein the antigen-specific IgA's are produced at a titer of at least about 1:100.

50. The method of claim 49, wherein the antigen-specific IgA's are produced at a titer of at least about 1:500.

51. The method of claim 30, wherein the immune response further comprises a cell-mediated immune response.

52. The method of claim 51, wherein the cell-mediated immune response comprises proliferation of lymphocytes.

53. The method of claim 52, wherein the proliferation of lymphocytes further comprises at least about a ten (10)-fold increase in lymphocytes as compared to an unimmunized state.

54. The method of claim 53, wherein the proliferation of lymphocytes further comprises at least about a fifty (50)-fold increase in lymphocytes as compared to an unimmunized state.

55. The method of claim 30, wherein the vertebrate subject is a mammal.

56. The method of claim 55, wherein the mammal is a human.

57. The method of claim 1, wherein the antigen-adjuvant composition further comprises a combination of at least two adjuvant molecules.

58. The method of claim 30, wherein the antigen-adjuvant composition further comprises a combination of at least two adjuvant molecules.

59. A method of eliciting an immune response against an antigen in a vertebrate subject, the method comprising:

(a) providing a water-soluble antigen-adjuvant composition comprising the antigen and IL-1β; and (b) administering said antigen-adjuvant composition intramucosally to the vertebrate subject in a manner such that initial contact occurs in mucosal tissue of the vertebrate subject, whereby an immune response is elicited.

60. The method of claim 59, wherein the antigen-adjuvant composition further comprises IL-1β in combination with at least one other cytokine.

61. The method of claim 60, wherein the immune response comprises a cell-mediated immune response.

62. The method of claim 61, wherein the cell-mediated immune response comprises proliferation of lymphocytes.

63. The method of claim 62, wherein the proliferation of lymphocytes further comprises at least about a ten (10)-fold increase in lymphocytes as compared to an unimmunized state.

64. The method of claim 63, wherein the proliferation of lymphocytes further comprises at least about a fifty (50)-fold increase in lymphocytes as compared to an unimmunized state.

* * * * *